United States Patent
Thiele

(10) Patent No.: US 10,028,682 B2
(45) Date of Patent: Jul. 24, 2018

(54) OXIDATION MEASUREMENT SYSTEM AND RELATED METHOD THEREOF

(71) Applicants: UNIVERSITY OF VIRGINIA PATENT FOUNDATION, Charlottesville, VA (US); Robert Thiele, Charlottesville, VA (US)

(72) Inventor: Robert H. Thiele, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 135 days.

(21) Appl. No.: 14/435,230

(22) PCT Filed: Oct. 12, 2013

(86) PCT No.: PCT/US2013/064737
§ 371 (c)(1),
(2) Date: Apr. 13, 2015

(87) PCT Pub. No.: WO2014/059399
PCT Pub. Date: Apr. 17, 2014

(65) Prior Publication Data
US 2015/0282747 A1  Oct. 8, 2015

Related U.S. Application Data

(60) Provisional application No. 61/713,291, filed on Oct. 12, 2012.

(51) Int. Cl.
*A61B 5/1455* (2006.01)
*A61B 5/1459* (2006.01)
(Continued)

(52) U.S. Cl.
CPC ........ *A61B 5/14552* (2013.01); *A61B 5/1459* (2013.01); *A61B 5/14546* (2013.01); *A61B 5/14551* (2013.01); *A61B 5/6852* (2013.01)

(58) Field of Classification Search
CPC .............. A61B 5/1455; A61B 5/14551; A61B 5/14552; A61B 5/6846; A61B 5/6847; A61B 5/6852; A61B 5/6853
See application file for complete search history.

(56) References Cited

U.S. PATENT DOCUMENTS

| | | |
|---|---|---|
| 4,281,645 A | 8/1981 | Jobsis |
| 5,125,888 A | 6/1992 | Howard |

(Continued)

FOREIGN PATENT DOCUMENTS

| | | |
|---|---|---|
| EP | 1547515 A1 | 6/2005 |
| WO | WO 90/07907 A1 | 7/1990 |

(Continued)

*Primary Examiner* — Eric Winakur
(74) *Attorney, Agent, or Firm* — Robert J. Decker

(57) ABSTRACT

A catheter system and related method for measuring the oxidation state of biological molecules in a region of a measurement site of a subject. The system may include a catheter device having one or more emitters in mechanical communication with the catheter and configured to make contact with a tissue wall of the subject. The catheter device also includes one or more detectors in mechanical communication with the catheter and configured to make contact with the tissue wall of the subject. The emitters and the detector are in electromagnetic radiation communication with one another, whereby the electromagnetic radiation communication allows visible radiation or near infrared radiation emitted by emitters to be detected by the detector to determine tissue oxidation state of the region of the measurement site of the subject.

70 Claims, 11 Drawing Sheets

(51) Int. Cl.
*A61B 5/145* (2006.01)
*A61B 5/00* (2006.01)

(56) References Cited

U.S. PATENT DOCUMENTS

| | | | |
|---|---|---|---|
| 5,423,772 A | 6/1995 | Lurie | |
| 5,597,377 A | 1/1997 | Aldea | |
| 5,707,335 A | 1/1998 | Howard | |
| 5,712,165 A | 1/1998 | Alvarez | |
| 5,715,816 A * | 2/1998 | Mainiero | A61B 5/1459 600/323 |
| 5,779,694 A | 7/1998 | Howard | |
| 5,916,153 A * | 6/1999 | Rhea, Jr. | A61B 5/1459 600/310 |
| 5,995,208 A | 11/1999 | Sarge | |
| 6,031,603 A | 2/2000 | Fine | |
| 6,216,030 B1 | 4/2001 | Howard | |
| 6,245,440 B1 | 6/2001 | Kuhlmann-Wilsdorf | |
| 6,272,370 B1 | 8/2001 | Gillies | |
| 6,298,259 B1 | 10/2001 | Kucharczyk | |
| 6,591,144 B2 | 7/2003 | Pigott | |
| 6,599,274 B1 | 7/2003 | Kucharczyk | |
| 6,626,902 B1 | 9/2003 | Kucharczyk | |
| 6,834,201 B2 | 12/2004 | Gillies | |
| 7,120,481 B2 | 10/2006 | Keller | |
| 7,435,229 B2 | 10/2008 | Wolf | |
| 7,670,327 B2 | 3/2010 | Kucharczyk | |
| 7,727,225 B2 | 6/2010 | Broaddus | |
| 8,073,517 B1 | 12/2011 | Burchman | |
| 8,096,984 B2 | 1/2012 | Kucharczyk | |
| 8,211,083 B2 | 7/2012 | Broaddus | |
| 8,216,228 B2 | 7/2012 | Pachon Mateos | |
| 8,226,694 B2 | 7/2012 | Broaddus | |
| 8,255,193 B2 | 8/2012 | Humphrey | |
| 8,282,565 B2 | 10/2012 | Mahapatra | |
| 8,328,420 B2 | 12/2012 | Abreu | |
| 8,406,837 B2 | 3/2013 | Gillies | |
| 8,655,798 B2 | 2/2014 | Humphrey | |
| 8,728,053 B2 | 5/2014 | Broaddus | |
| 8,888,737 B2 | 11/2014 | Vaisnys | |
| 8,906,056 B2 | 12/2014 | Gillies | |
| 9,211,405 B2 | 12/2015 | Mahapatra | |
| 9,218,752 B2 | 12/2015 | Gillies | |
| 9,314,265 B2 | 4/2016 | Mahapatra | |
| 9,339,221 B1 * | 5/2016 | Heaton, II | A61B 5/1459 |
| 9,468,396 B2 | 10/2016 | Mahapatra | |
| 9,636,487 B2 | 5/2017 | Utz | |
| 9,642,534 B2 | 5/2017 | Mahapatra | |
| 9,669,198 B2 | 6/2017 | Broaddus | |
| 2001/0024735 A1 | 9/2001 | Kuhlmann-Wilsdorf | |
| 2002/0103430 A1 | 8/2002 | Hastings | |
| 2003/0236647 A1 | 12/2003 | Yoon | |
| 2004/0111016 A1 | 6/2004 | Casscells, III | |
| 2005/0119556 A1 | 6/2005 | Gillies | |
| 2005/0187488 A1 | 8/2005 | Wolf | |
| 2007/0078500 A1 | 4/2007 | Ryan | |
| 2008/0262467 A1 | 10/2008 | Humphrey | |
| 2009/0048577 A1 | 2/2009 | Gillies | |
| 2009/0105605 A1 | 4/2009 | Abreu | |
| 2009/0192487 A1 | 7/2009 | Broaddus | |
| 2010/0094143 A1 | 4/2010 | Mahapatra | |
| 2010/0114093 A1 | 5/2010 | Mahapatra | |
| 2010/0210927 A1 | 8/2010 | Gillies | |
| 2010/0211064 A1 | 8/2010 | Mahapatra | |
| 2010/0241185 A1 | 9/2010 | Mahapatra | |
| 2011/0092951 A1 | 4/2011 | Vaisnys | |
| 2011/0295177 A1 | 12/2011 | Mohl | |
| 2012/0123461 A1 | 5/2012 | Gillies | |
| 2012/0283582 A1 | 11/2012 | Mahapatra | |
| 2012/0310052 A1 | 12/2012 | Mahapatra | |
| 2012/0330184 A1 | 12/2012 | Mahapatra | |
| 2013/0085386 A1 | 4/2013 | Humphrey | |
| 2013/0090556 A1 | 4/2013 | Broaddus | |
| 2013/0096428 A1 | 4/2013 | Gillies | |
| 2013/0108999 A1 | 5/2013 | Gillies | |
| 2013/0225904 A1 | 8/2013 | Gillies | |
| 2013/0295192 A1 * | 11/2013 | Hirsch | A61B 5/14551 600/479 |
| 2013/0303967 A1 | 11/2013 | Utz | |

FOREIGN PATENT DOCUMENTS

| | | |
|---|---|---|
| WO | WO 97/37847 A1 | 10/1997 |
| WO | WO 00/07652 A1 | 2/2000 |
| WO | WO 00/23000 A1 | 4/2000 |
| WO | WO 02/074358 A2 | 9/2002 |
| WO | WO 03/035139 A2 | 5/2003 |
| WO | WO 2005/060825 A1 | 7/2005 |
| WO | WO 2006/015091 A2 | 2/2006 |
| WO | WO 2006/089243 A2 | 8/2006 |
| WO | WO 2006/113267 A2 | 10/2006 |
| WO | WO 2007/050487 A2 | 5/2007 |
| WO | WO 2007/081842 A2 | 7/2007 |
| WO | WO 2008/002595 A2 | 1/2008 |
| WO | WO 2008/013709 A2 | 1/2008 |
| WO | WO 2008/112870 A2 | 9/2008 |
| WO | WO 2008/115745 A2 | 9/2008 |
| WO | WO 2008/118737 A1 | 10/2008 |
| WO | WO 2009/062061 A1 | 5/2009 |
| WO | WO 2010/127259 A1 | 11/2010 |
| WO | WO 2011/066429 A1 | 6/2011 |
| WO | WO 2011/102874 A1 | 8/2011 |
| WO | WO 2011/103456 A2 | 8/2011 |
| WO | WO 2011/160080 A1 | 12/2011 |
| WO | WO 2014/047179 A1 | 3/2014 |

* cited by examiner

OXIDATION MEASUREMENT SYSTEM AND RELATED METHOD THEREOF

RELATED APPLICATIONS

The present application is a national stage filing of International Application No. PCT/US2013/064737, filed Oct. 12, 2013, which claims priority under 35 U.S.C.§ 119(e) from U.S. Provisional Application Ser. No. 61/713,291, filed Oct. 12, 2012, entitled "Oximetric Coronary Sinus Catheter and Related Method thereof," the disclosures of which are hereby incorporated by reference herein in their entirety.

TECHNICAL FIELD

The present invention relates generally to the field of oximetric catheters and other medical devices. More specifically, the present invention also relates to improving the measurement of the oxidation state of biological molecules (such as determining the oxidation status of hemoglobin) in the myocardium or other region of the measurement site.

BACKGROUND

The vast majority of modern cardiac surgical operations require cardiopulmonary bypass, which was developed in the 1950s, in order to be performed safely. During cardiopulmonary bypass, large cannulas are inserted into the arterial and venous systems (usually via the aorta and the vena cevae). The cardiopulmonary bypass machine removes deoxygenated blood from the body via the vena cevae, adds oxygen to the blood, and returns it to the circulation by pumping it into the aorta. An aortic "cross clamp" is placed in between the heart and the brachiocephalic artery, which assures that no blood from the aortic cannula enters into the heart, thereby providing the surgeon with a "bloodless field."

Under normal circumstances this series of events would lead to rapid deoxygenation and death of myocardial tissue. However, cardiac surgeons, with the help of clinical perfusionists, inject cardioplegia solution into the coronary arteries. Cardioplegia solution is a mixture of cold blood and a variety of other substances (e.g. potassium), which perform three critical functions—1) cool the myocardium [which decreases its consumption of oxygen] 2) stop the myocardium from contracting [which also decreases its consumption of oxygen] 3) deliver oxygen to the heart. Cardioplegia is injected approximately every twenty minutes and requires cessation of the operation (because during cardioplegia injection, the heart fills with cardioplegia). While the purpose of cardioplegia is to provide myocardial protection, there is no way to reliably assess its adequacy. Currently, surgeons rely on 1) visualizing mechanical myocardial contraction and 2) visualizing electrical activity on the electrocardiogram (ECG), both of which suggest that the heart is beginning to contract despite its deoxygenated state.

If perfusion is inadequate, patients may suffer irreversible myocardial damage which can lead to either a need for heart transplantation or death. While this occurs rarely, it is a known complication of cardiac surgery.

In patients with significant coronary artery disease, left ventricular hypertrophy, or aortic valve insufficiency, it may be difficult to adequately protect the myocardium by injecting cardioplegia solution through the coronary arteries (the "anterograde" approach). In these cases, surgeons will often place a catheter in the coronary sinus (a large vein which drains the heart) and inject cardioplegia solution into the myocardium in a "retrograde" fashion. This is referred to as "retrograde cardioplegia."

Overview

The coronary sinus is a unique anatomical structure as it wraps around the left ventricle. An aspect of an embodiment of the present invention provides for the placement of a tissue oxygen monitor on the coronary sinus that would allow the surgeon to monitor the oxygenation status of the left ventricle.

A purpose of an embodiment of the present invention oximetric coronary sinus catheter device and related method is to, but not limited thereto, provide cardiac surgeons, cardiac anesthesiologists, and clinical perfusionists with a means of assessing the oxygenation status of the myocardium during cardiopulmonary bypass for cardiac surgery. Alternatively, a purpose of an embodiment of the present invention pulmonary artery catheter device and related method is to, but not limited thereto, provide cardiac surgeons, cardiac anesthesiologists, and clinical perfusionists with a means of assessing the oxygenation status of the myocardium of the right ventricle during cardiopulmonary bypass for cardiac surgery. Currently there are no clinically available means for assessing myocardial oxygenation during cardiac surgery.

An aspect of an embodiment of the present invention relies on visible spectroscopy (covering a spectrum of approximately 380 to approximately 750 nm) and/or near infrared spectroscopy (NIRS, in which absorbance of electromagnetic radiation in the near infrared [approximately 700 to approximately 1,100 nm] range is utilized to measure non-pulsatile tissue oxygenation status) to estimate the oxygen content of the myocardium. It should be appreciated that the spectroscopy range may also be at a level lower than 380 nm and/or a level greater than 1100 nm as desired, needed or required for operation and effectiveness.

Coronary sinus catheters are generally used by cardiac surgeons to deliver cardioplegia to the heart during surgery.

An aspect of an embodiment of the present invent device provides, among other things, a significant feature/approach that will allow cardiac surgeons, cardiac anesthesiologists, and clinical perfusionists to assess the adequacy of cardioplegia/myocardial protection.

An aspect of an embodiment of the present invention device and method is, but not limited thereto, that it will allow cardiac surgeons, cardiac anesthesiologists, and clinical perfusionists to implement "retrograde cardioplegia" while reducing the risk to the patient and with no additional procedural time.

While some dimensions may be provided or illustrated on the figures or within the description, it should be appreciated that the device may constitute various sizes, dimensions, contours, rigidity, shapes, flexibility and materials as it pertains to the components or portions of components of the device, and therefore may be varied and utilized as desired or required to meet the anatomical and structural demands, operational requirements, and surgical and clinical needs.

It should be appreciated that the related components or portions of the related components as discussed herein may take on all shapes along the entire continual geometric spectrum of manipulation of x, y and z planes to provide and meet the anatomical and structural demands, operational requirements, and surgical and clinical needs.

An aspect of an embodiment of the present invention provides, but not limited thereto, a system for measuring the oxidation state of biological molecules in a region of a measurement site of a subject. The system may comprise: at least one emitter configured to be in optical communication with the region of the measurement site of the subject; at least one detector configured to be in optical communication with the region of the measurement site of the subject; wherein the at least one emitter or the at least one detector is configured to be disposed inside the subject; and the at least one emitter and the at least one detector are in electromagnetic radiation communication with one another, wherein the electromagnetic radiation communication allows visible radiation or near infrared radiation emitted by the at least one emitters to be detected by the at least one detector to determine tissue oxidation state of the region of the measurement site of the subject. Moreover, the system may be configured wherein both the at least one emitter and the at least one detector are configured to be disposed inside the subject. It should be appreciated that the at least one emitter may be an array of emitters or a plurality of emitters or the like. Similarly, it should be appreciated the at least one detector may be an array of detectors or a plurality of detectors or the like.

An aspect of an embodiment of the present invention provides, but not limited thereto, a catheter system for measuring the oxidation state of biological molecules in a region of a measurement site of a subject. The system may comprise: a catheter device having a lumen, the catheter device includes proximal region, a distal regional, and a longitudinal region there between; at least one emitter in mechanical communication with the catheter distal region and configured to make contact with a tissue wall of the subject; at least one detector in mechanical communication with the catheter distal region and configured to make contact with the tissue wall of the subject; and the at least one emitter and the at least one detector are in electromagnetic radiation communication with one another, wherein the electromagnetic radiation communication allows visible radiation or near infrared radiation emitted by the at least one emitters to be detected by the at least one detector to determine tissue oxidation state of the region of the measurement site of the subject. Moreover, the system may comprise an expandable component in mechanical communication with the catheter distal region, and located between the at least one emitter and the at least one detector and the catheter distal region.

An aspect of an embodiment of the present invention provides, but not limited thereto, a method for measuring the oxidation state of biological molecules in a region of a measurement site of a subject. The method may comprise: providing at least one emitter in optical communication with the region of the measurement site of the subject; providing at least one detector in optical communication with the region of the measurement site of the subject; disposing the at least one emitter or the at least one detector inside the subject; and communicating electromagnetic radiation between the at least one emitter and the at least one detector, wherein the electromagnetic radiation communication allows visible radiation or near infrared radiation emitted by the at least one emitters to be detected by the at least one detector to determine tissue oxidation state of the region of the measurement site of the subject. Moreover, the method may comprise disposing both the at least one emitter and the at least one detector inside the subject.

An aspect of an embodiment of the present invention provides, but not limited thereto, a method for measuring the oxidation state of biological molecules in a region of a measurement site of a subject. The method may comprise: providing a catheter device having a lumen, the catheter device includes proximal region, a distal regional, and a longitudinal region there between; providing at least one emitter configured to make contact with a tissue wall of the subject; providing at least one detector configured to make contact with the tissue wall of the subject; and communicating electromagnetic radiation between the at least one emitter and the at least one detector, wherein the electromagnetic radiation communication allows visible radiation or near infrared radiation emitted by the at least one emitters to be detected by the at least one detector to determine tissue oxidation state of the region of the measurement site of the subject. Moreover, the method may comprise providing an expandable component in mechanical communication with the catheter distal region, and located between the at least one emitter and the at least one detector and the catheter distal region.

A catheter system and related method for measuring the oxidation state of biological molecules in a region of a measurement site of a subject. The system may include a catheter device having one or more emitters in mechanical communication with the catheter and configured to make contact with a tissue wall of the subject. The catheter device also includes one or more detectors in mechanical communication with the catheter and configured to make contact with the tissue wall of the subject. The emitters and the detector are in electromagnetic radiation communication with one another, whereby the electromagnetic radiation communication allows visible radiation or near infrared radiation emitted by emitters to be detected by the detector to determine tissue oxidation state of the region of the measurement site of the subject. Moreover, the system may include an expandable component in communication with the catheter device configured to assure that the at least one emitter and the at least one detector makes contact with the tissue wall.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

Figure 1A:
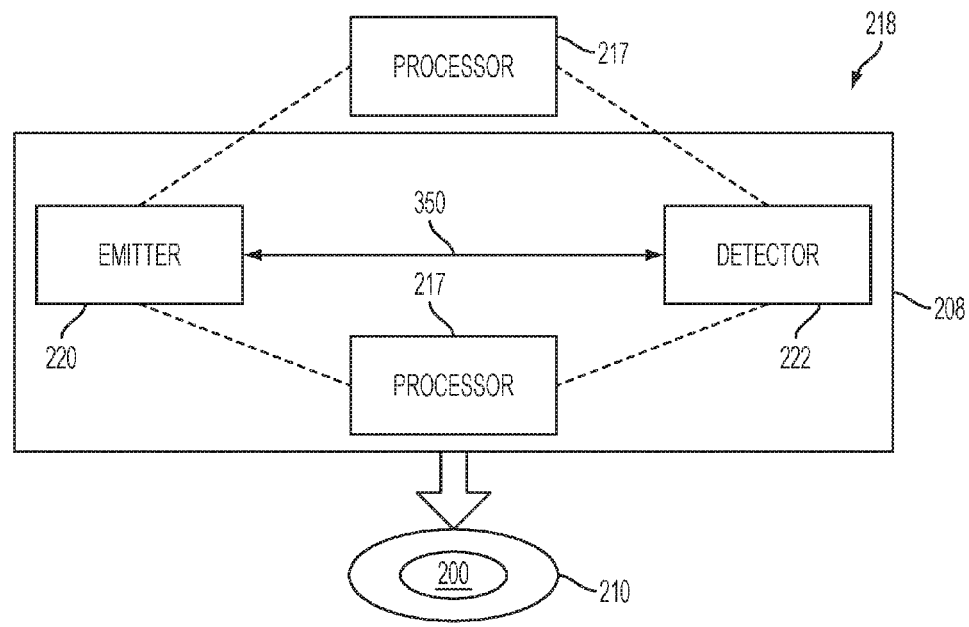
FIG. 1 provides a schematic diagram of a system for measuring the oxidation state of biological molecules in a region of a measurement site whereby the interface member exists as a single component (FIG. 1A) or multiple components (FIG. 1B).

FIG. 1 provides a schematic diagram of a system 218 for measuring the oxidation state of biological molecules in a region of a measurement site 200 of a subject 210. The oxidation measurement system 218 may comprise at least one emitter 220 that may be configured to be in optical communication with the region of the measurement site 200 of the subject 210. Additionally, at least one detector 222 may be configured to be in optical communication with the region of the measurement site 200 of the subject 210. Additionally, the at least one emitter 220 and the at least one detector 222 are in electromagnetic radiation communication 350 (e.g., optically coupled) with one another, wherein the electromagnetic radiation communication allows visible radiation or near infrared radiation emitted by said at least one emitters 220 to be detected by said at least one detector 222 to determine tissue oxidation state of the biological molecules of the region of the measurement site 200 of the subject 222. Moreover, the at least one emitter 220 and said at least one detector 222 is in communication with a processor 217. As shown in FIG. 1A, an interface member 208 may be provided whereby the at least one emitter 220 and at least one detector 222 are in mechanical communication (directly or indirectly) with the common interface member 208. An example of an interface member 208 is a catheter, substrate, probe, patch, drain, guidewire, tube, drainage tube, conduit, elongated member, lumen, circuit board, encapsulant, casing, housing, packaging, ultrasound device, or membrane. For example, but not limited thereto, if the interface member is an ultrasound device then it may be in the form of an esophageal Doppler or transesophageal echocardiogram (TEE) probe. It should be appreciated that the processor 217 may be in mechanical communication (directly or indirectly) with the interface member 208 or in non-mechanical communication with the interface member 208. Alternatively, the processor may exist in multiple modules (housings, packaging, or encasings) and therefore may be in both mechanical and non-mechanical communication with the interface member 208. Moreover, the interface member may be implemented with or as a part of the subject's attire, such as but not limited thereto, glasses, watch, jewelry, head bands, waistbands, other bands or straps, hat, clothing, undergarments, belts, hats, helmets, etc.

Figure 1B:
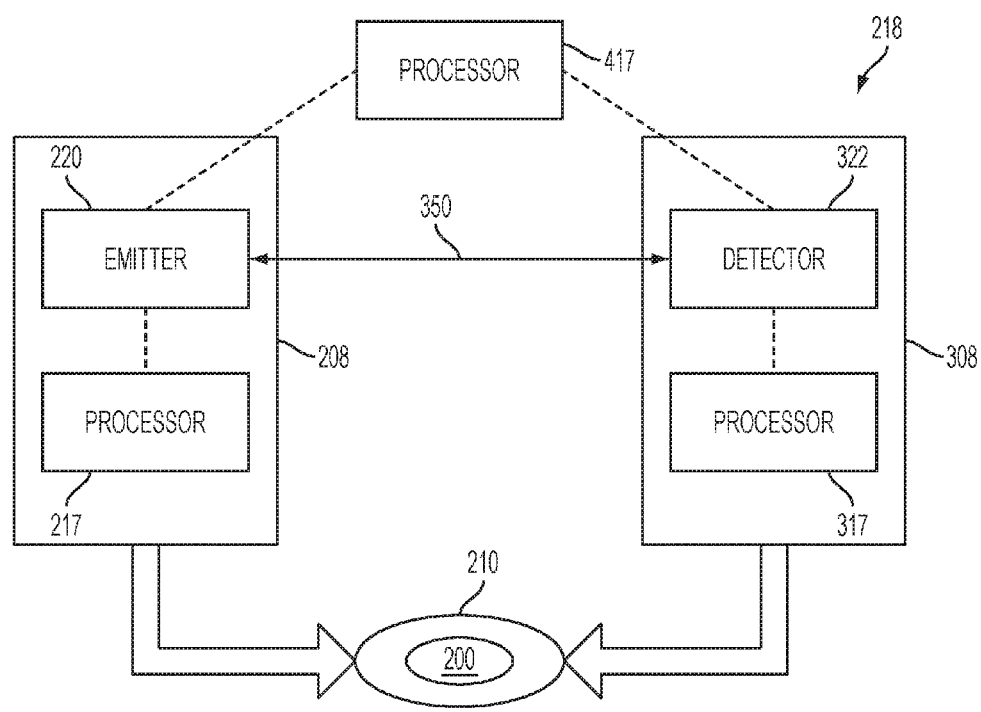

Turning to FIG. 1B, the measurement system 218 is similar to that illustrated in FIG. 1A except for the interface member 208 exists in two or more separate components or modules. Again, an interface member may be a catheter, substrate, probe, patch, drain, guidewire, lumen, or membrane. It should be appreciated that a processor 217 may be in mechanical communication (directly or indirectly) with an interface member 208 and/or a processor 317 may be in mechanical communication with the other interface member 308. Alternatively or in addition thereto a processor 417 may be in non-mechanical communication with the interface members.

An aspect of an embodiment of the measurement system 218 may be used for, but not limited thereto, measuring the oxidation state of a variety of anatomy locations of the subject. For instance, the an aspect of an embodiment of the measurement system 218 may be used for, but not limited thereto, measuring the oxidation state a variety of intended targets, such as the heart, other organs, tissues, muscles, and blood. Still yet, an aspect of an embodiment of the measurement system 218 may be used for, but not limited thereto, measuring the oxidation state of a variety of regions such as, but not limited thereto, thoracic region, abdominal region, and pelvic region, as well as limbs, skull region and brain.

Moreover, an embodiment of the measurement system 218 (or any portions thereof) may be disposed internally (in vivo) in the subject or disposed externally (ex vivo) to the subject. Similarly, for an embodiment of the measurement system 218 (or any portions thereof) it may be a mixed combination whereby some portions are internally (in vivo) disposed in the subject and some portions are externally (ex vivo) disposed to the subject.

Moreover, an embodiment of the measurement system 218 (or any portions thereof) may be inserted or disposed through a percutaneous venous entry or other incision, or maybe inserted or disposed through the mouth, eye, or ear. For example, the measurement system 218 (or any portions thereof) may be inserted into the esophagus of the subject.

Still yet, an aspect of an embodiment of the measurement system 218 may be used for, for measuring the oxidation state of biological molecules in a region of a measurement site of a subject 210. The biological molecules may be at least one of the following types: Hemoglobin, myoglobin, or cytochrome. The biological molecules may be in at least one of the following: muscle, organs, or tissue (which would include blood).

Figure 2:
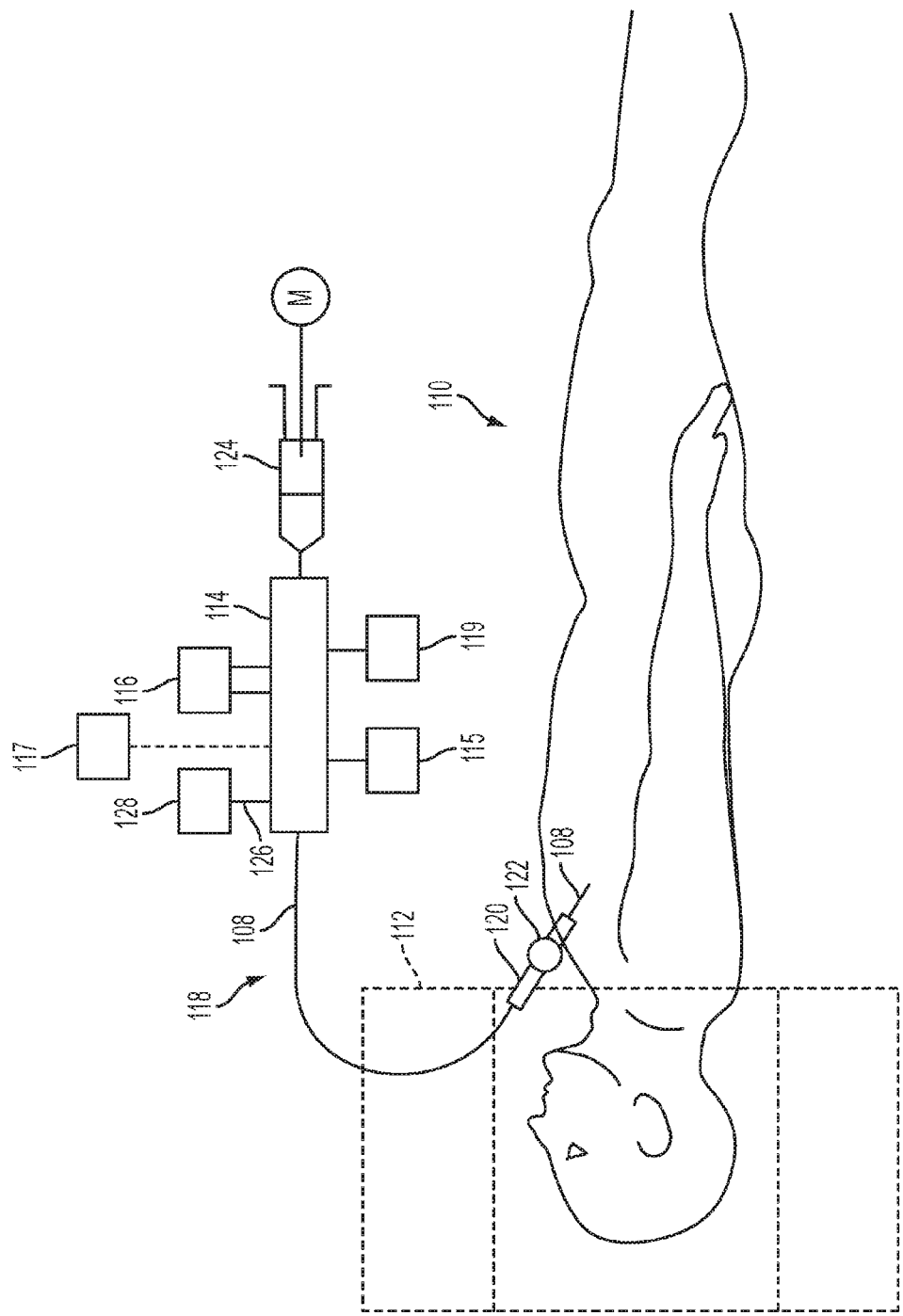
FIG. 2 provides a schematic diagram showing a patient (or any subject) for examination and/or intervention with a catheter, such as an oximetric coronary sinus catheter whereby a catheter device is disposed within the patient. It should be appreciated that (although not specifically shown) the catheter device may be a pulmonary artery catheter or other type. It may be a catheter, lumen, channel, conduit, drain, sheath, stent, probe, or guidewire. Similarly, other than being a generally elongated member it may be any shape, such as, but not limited thereto membrane, patch, substrate, casing, board, circuit board, electronics, module or any type of implant or insert.

FIG. 2 provides an exemplary embodiment of the present invention oxidation measurement system that includes an interface member. For instance, FIG. 2 provides a schematic diagram showing a patient 110, or any subject for examination and/or intervention with an interface member that in the instant illustration is a catheter 108, such as an oximetric coronary sinus catheter as part of a catheter system 118, whereby the catheter device is disposed within the patient.

Still referring to FIG. 2, a manifold 114 may couple several therapeutic or diagnostic devices or systems typified by device 116 to the catheter system 118. An electromagnetic radiation source (e.g., visible or infrared radiation) 115 is provided, such as in a near infrared spectroscopy (NIRS) system/device. For example, an optical fiber or the like may be provided for transmission. Additionally, a syringe, flow-driver and/or pumping device 124 may also be in communication with the manifold 114. The catheter device 108 in turn may be delivered through a guide sheath 120 that may be positioned in a navigation guide 122. Also, a computer or processor 117 (as well as displays, output devices, input devices, printers, and computer storage) may be in communication with the catheter device or catheter system. Any computer or processor may be located locally or remotely, or a combination thereof. It should be appreciated that aspects of the spectroscopy system/device may be at the manifold end (e.g., the proximal location or other desired location) and span to the catheter distal end (or other desired location). Alternatively, the aspects may be self-contained at the distal end, whereby various emitters and detectors, etc. are located at the distal end of the catheter or the like.

For example, in operation the physician or user inserts the catheter device 108 into the heart (or other anatomy part or subject region) under fluoroscopic guidance or other applicable examination or intervention. The same or similar visualization may be used to follow the progress of the implant both acutely and chronically. This specific version of the catheter within the concepts disclosed herein may have a main catheter, or may have an outer catheter/tube with an inner catheter/tube as well. This main catheter device may also have various interior and peripheral lumens, chambers, conduits, and channels that will also be discussed in greater detail herein, within the context of the disclosure provided. Such interior and peripheral lumens, chambers, conduits, and channels may be used to deliver other devices and perform various diagnostic functions. For example, each lumen, chamber, conduits, and channel may communicate with a separate port of the manifold 114. A lumen, chamber, conduit, or channel may contain a pressure transducer 128. Other lumens, chambers, conduits and channels may be devoted to an optical cell counter device, for example, as shown generically as device 119 in FIG. 1. Such a cell counter device (for example a cytometry or similar) may operate with two fibers located in two separate lumens and/or ports to measure the number of and viability of cells delivered by the catheter. An example of fiber optics related application/technology is discussed in U.S. Pat. No. 8,096,984 B2 to Kucharczyk et al, of which is hereby incorporated by reference herein in its entirety.

Optionally, the subject 118 or object may undergo an examination and/or an intervention procedure inside the bore of an MRI system 112 (or other imaging modality); and while the catheter system 118 or catheter device 108 is disposed within the patient 110. For instance, in operation the physician or user inserts the catheter device 108 into the heart (or other anatomy part or subject region) under MRI guidance or other applicable examination or intervention. Alternatively, the imaging may occur subsequently or prior to catheter guidance. Therefore, the imaging may take place before, during or after (or any combination) to a relevant procedure/operation—or omitted altogether. It should be appreciated that while an MRI related system is depicted, a variety of systems and methods may implemented within the spirit of the present invention including, but not limited thereto, the following: computed tomography (CT), fluoroscopy, ultrasound, PET scanning, nuclear medicine camera, other radiological systems, or other biomedical imaging techniques and methods.

It should be appreciated, that as discussed herein a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog), etc. It should be appreciated that the subject may be any applicable patient, for example.

It should be appreciated that an aspect of an embodiment of the present invention provides, but not limited thereto, a computer planning workstation (and any related computer system, processor, PDA, laptop, computer notebook, method and computer readable medium as required, needed or desired) that may be used to, but not limited thereto, calculate the coordinates necessary for catheter insertion (e.g., stereotactic coordinates) and maneuvering, or for displaying information or data derived from the catheter device and system in general.

It should be appreciated that various computer systems, methods and computer readable media as required, needed or desired may be implemented and practiced according to any of the demands, techniques, or objectives of the various embodiments of the present invention disclosed herein.

It should be appreciated that any of the components or modules referred to with regards to any of the present invention embodiments disclosed in FIGS. 1 and 2 (for example) and discussed herein and other figures, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

The term "processor" may include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor. The functional aspects may include performing an operation or instruction or providing controls for the various systems and devices (or portions thereof) disclosed herein—or other functions as desired, needed or required. The term "processor" may include any analog, mechanical, or electro-mechanical device, equipment or component for performing an operation or instruction or providing controls (such as a controller) for the various systems and devices (or portions thereof) disclosed herein—or other functions as desired, needed or required.

Figure 3A:
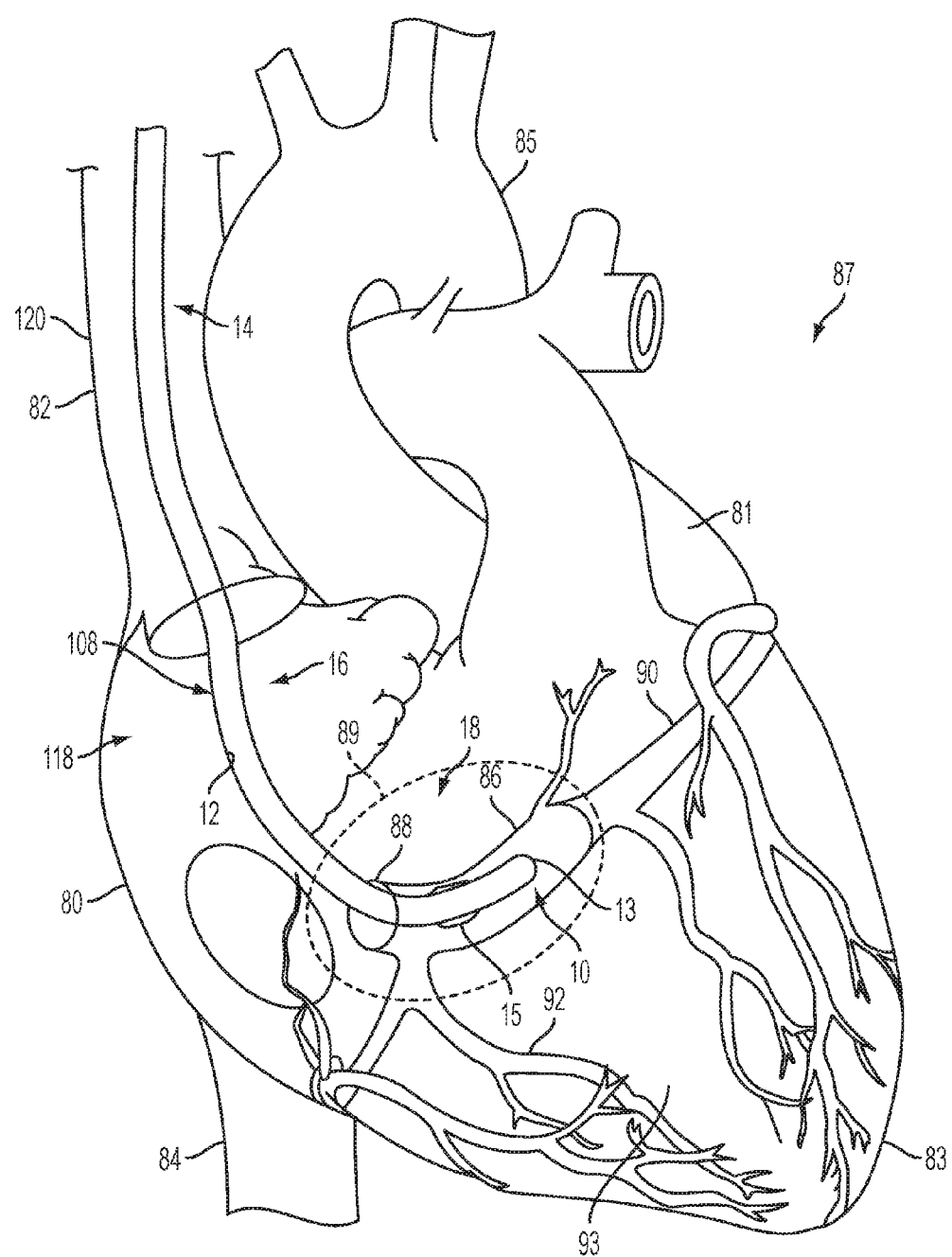
FIG. 3A provides a schematic elevation view of a catheter device, such as oximetric coronary sinus catheter maneuvered into the coronary sinus.

FIG. 3A provides an exemplary embodiment of the present invention oxidation measurement system that includes an interface member. For instance, FIG. 3A provides a schematic elevation view of an interface member that in the instant illustration is a catheter device 108, such as oximetric coronary sinus catheter, of a catheter system 118 positioned with the patient's heart 87. The catheter device 108 may be used for, but not limited thereto, measuring the oxygenation status of a region of subject. In an approach, the region may be the myocardium 89 that is located, for example, in the left ventricle of the heart. The catheter 108 may be inserted through a percutaneous venous entry, such as though the jugular vein, and the distal tip 13 is guided through the superior vena cava 82 optionally using a sheath 120 or the like, and then is further guided through the right atrium 80 maneuvered into the coronary sinus 86. It should be appreciated that a percutaneous venous entry may also include, for example, the femoral vein or subclavian vein. It should be appreciated that in other techniques, the catheter device 108 may be inserted through the other regions or vasculature, such as inferior vena cava 84, left atrium 81 or the aorta 85. Also provided in the representative illustration of the heart are: left ventricle 83, inferior vena cava 84, aorta 85, coronary sinus ostium 88, myocardium 89, large coronary vein 90, and small coronary vein 92. The catheter device 108 includes a lumen 12 (not shown) whereby the catheter device includes proximal region 14, a distal regional 18, and a longitudinal region 16 there between. At least one emitter 20 (not shown in instant figure due to limitations of the size of the illustration) is provided by any available means to achieve mechanical communication with the catheter distal region and configured to make contact with a tissue wall, such as of the coronary sinus 86. Further, at least one detector 22 (not shown in instant figure due to limitations of the size of the illustration) is provided by any available means to achieve mechanical communication with the catheter distal region and configured to make contact with the tissue wall, such as of the coronary sinus 86.

It should be appreciated that the one or more emitters or one or more detectors may include a plurality of emitters and detectors, respectively. Further, the emitters may be in contact with the expandable components or the walls of the catheter device, or both.

Alternatively, the catheter device 108, such as pulmonary artery catheter embodiment the catheter system 118, may be positioned with the patient's heart 87 and configured to make contact with the tissue wall, such as of the right ventricle.

Alternatively, the catheter device 108, may be used for procedure other than with the heart, such that it may be utilized as an abdominal drain.

Figure 3B:
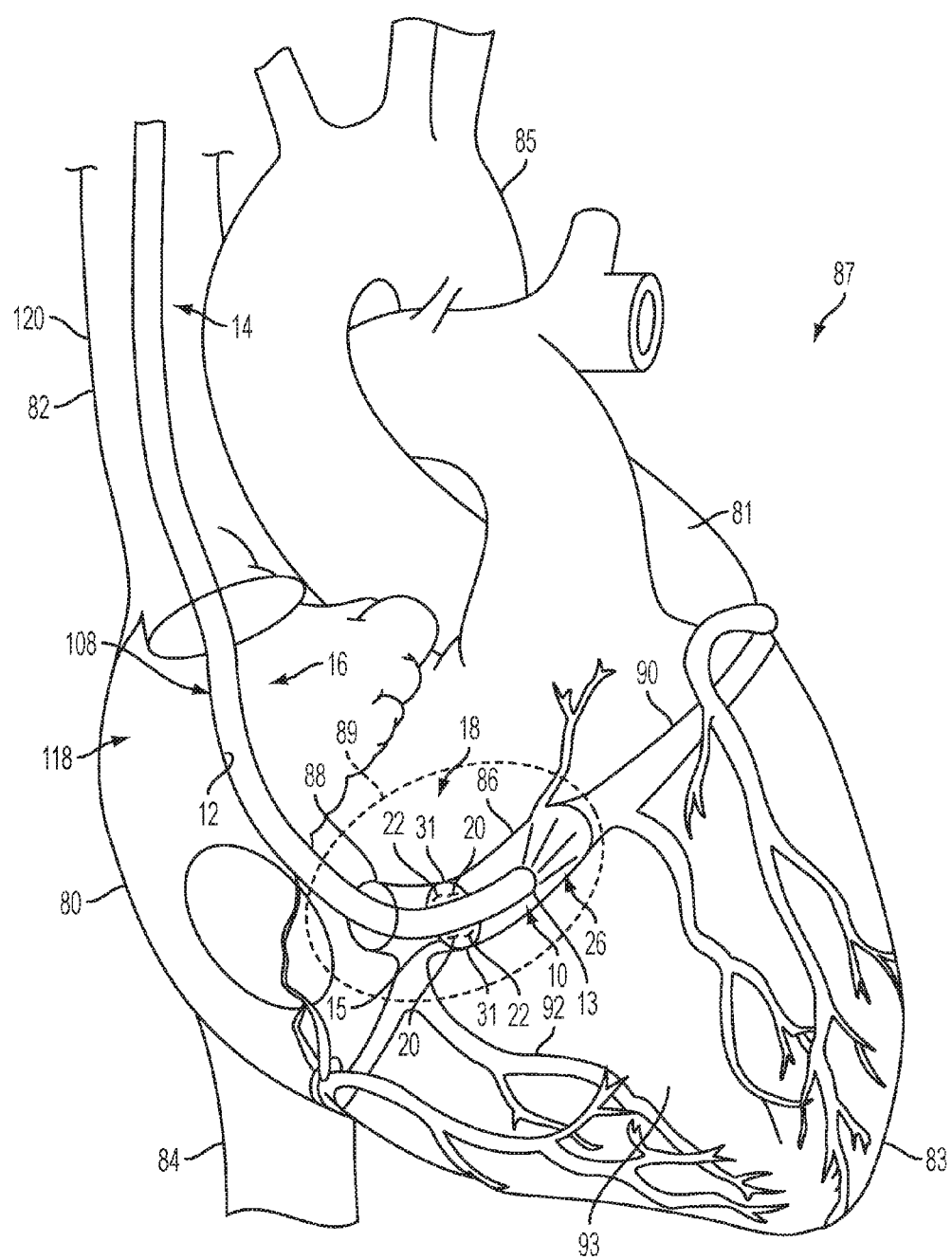
FIG. 3B provides the same view as FIG. 3A but for the expandable component is in an expanded, deployed or actuated position; and the cardioplegia solution is being dispensed from (delivered from) the catheter device.

FIG. 3B provides the same view as FIG. 3A but for the expandable component that is in an expanded, deployed or actuated position and the cardioplegia solution is being dispensed from (or delivered from) the catheter device. Also, at least one emitter 20 and the at least one detector 22 are within view according the instant figure. Further yet, the at least one emitter 20 and the at least one detector 22 are in electromagnetic radiation communication with one another, wherein the electromagnetic radiation communication allows near infrared radiation emitted by said at least one emitters to be detected by said at least one detector to determine tissue oxygenation of the region of the subject. The catheter 108 may further include an expandable component 15 that may be in mechanical communication with said catheter distal region. The expandable component 15 is essentially situated so as to be between the emitter and detector and catheter distal region. For instance, the expandable component 15 is configured to assure that said at least one emitter 20 and said at least one detector 22 makes contact with the tissue wall of the coronary sinus 86 or the like, such as at the illustrated contact region 31. The expandable component 15 may be at least one of the following: a balloon, expandable structure, or inflatable compartment. The emitters 20 and detector 20 may be in communication with a processor or computer, or the like (as shown for example in FIG. 1). At least one port 13 may be in communication with said catheter distal region (as well as other regions as desired, needed or required). The port may be configured for delivering cardioplegia solution 26 (as well as other material, medium, fluid, or agents). Moreover, it may be configured for delivering or withdrawing, or some combination. In an approach, the catheter device may include at least one port disposed on said distal tip. Again, the port at the distal tip is configured for delivering cardioplegia solution 26 (as well as other material, medium, fluid, or agents). Moreover, it may be configured to deliver or withdraw, or a combination.

The processor (for example shown in FIGS. 1 and 2) may be configured to perform the algorithmic steps to determine the tissue oxygenation ($StO_2$) of the region of the subject. The tissue oxygenation ($StO_2$) of the region of the subject is accomplished using Bee-Lambert law or empirical derivation.

For instance, in an approach, at least two emitters are provided; wherein one of said emitters is configured to emit the electromagnetic radiation at a high frequency so as to be above an isobestic point and one of said emitters is configured to emit the electromagnetic radiation at a low frequency so as to below the isobestic point. Additionally, at least four detectors are provided whereby the four detectors are located in communication with said catheter distal region so as to be at a known predetermined distance from respective said at least two emitters. Accordingly, two detectors are provided for each of the referenced high and low frequencies of the emitters. The two emitters and four detectors are in communication with the processor. The processor is configured to perform the algorithmic steps to determine the tissue oxygenation ($StO_2$) of the region of the subject. For example, the tissue oxygenation ($StO_2$) is determined by the execution of the following formula:

$$StO_2 = f(\text{high frequency}_{near}, \text{high frequency}_{far}/\text{low frequency}_{near}, \text{low frequency}_{far}).$$

Figure 4A:
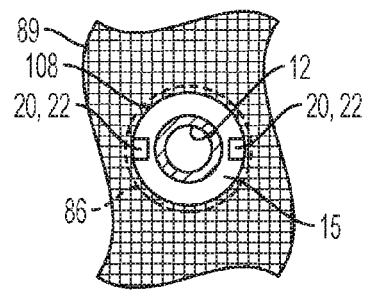
FIG. 4A provides a schematic cross-sectional view of a catheter device, such as oximetric coronary sinus catheter, having expandable component and emitters and detectors that are within a vasculature such as the coronary sinus surrounded by the myocardium.

FIG. 4A provides an exemplary embodiment of the present invention oxidation measurement system that includes an interface member. For instance, FIG. 4A provides a schematic cross-sectional view of an interface member that in the instant illustration is a catheter device 108, such as oximetric coronary sinus catheter, having a lumen 12, an expandable component 15 and emitters 20 and detectors 22 that are within a vasculature (or in contact with targeted tissue, for example) such as the coronary sinus 86 surrounded by the myocardium 89.

Figure 4B:
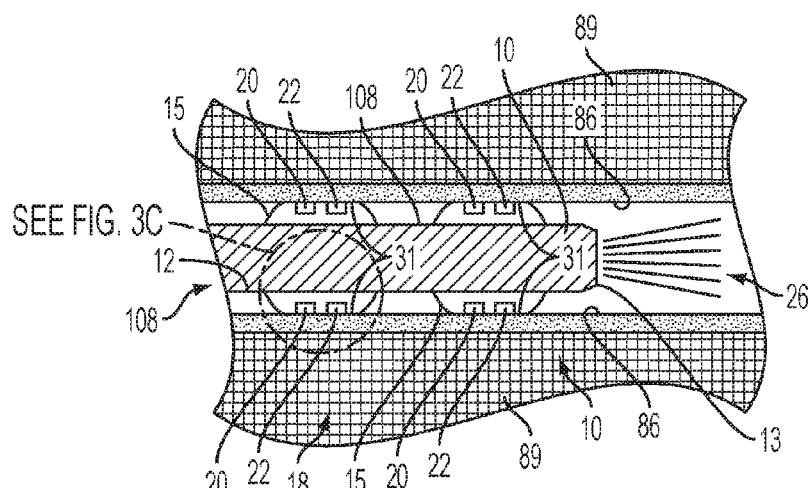
FIG. 4B provides a schematic longitudinal elevation view of a catheter device, such as oximetric coronary sinus catheter, having expandable component (in expanded, deployed, or actuated position) and emitters and detectors that are within a vasculature such as the coronary sinus surrounded by the myocardium whereby cardioplegia solution is being dispensed.

FIG. 4B provides a schematic longitudinal elevation view of the catheter device 108 shown in FIG. 4B, having a lumen 12, an expandable component (in expanded, deployed or actuated position) 15 and emitters 20 and detectors 22 that are within a vasculature (or in contact with targeted tissue, for example) such as the coronary sinus 86 surrounded by the myocardium 89 whereby cardioplegia solution 26 is being dispensed or delivered to the target of interest. The expandable component (in expanded, deployed or actuated position) 15 are provided to keep the emitters 20 and detectors 22 in contact with the vasculature (i.e. tissue wall), such as the coronary sinus 86. The contact with the vasculature may be, for example, as the illustrated by the contact region 31. It should be appreciated that the expandable component may also be utilized to provide a seal so as to prevent or mitigate any material, fluid, or agents from passing outside the catheter either in a proximal longitudinal direction or distal longitudinal direction or both.

Figure 4C:
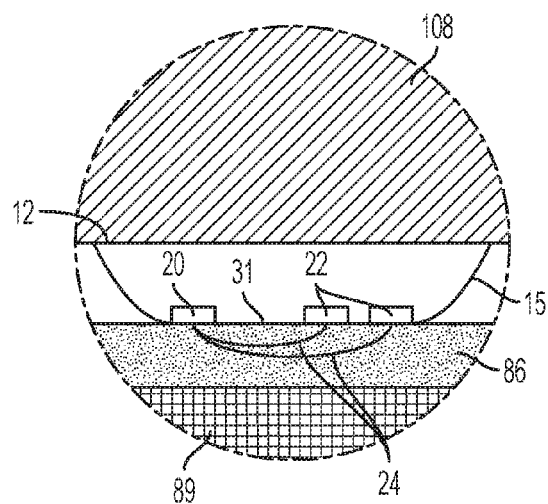
FIG. 4C provides an enlarged partial view of the catheter provided in FIG. 4B.
Figure 5A:
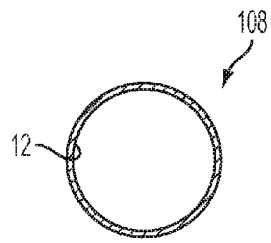
FIG. 5 provides a schematic exemplary cross-sectional view of various embodiments of the catheter device.
Figure 5B:
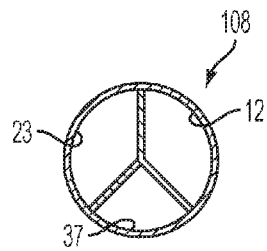
Figure 5C:
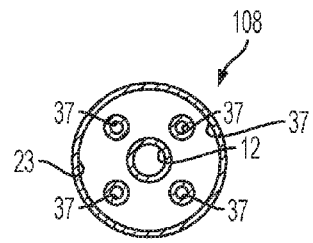
Figure 5D:
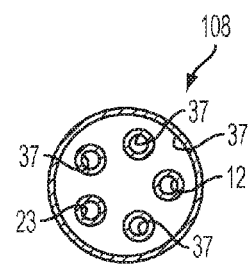
Figure 5E:
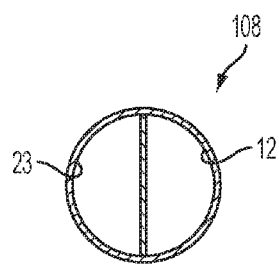
Figure 5F:
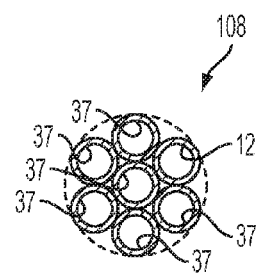
Figure 5G:
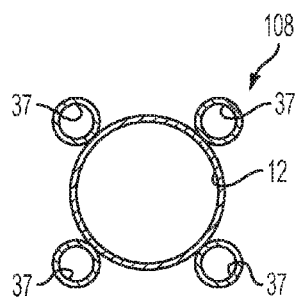
Figure 5H:
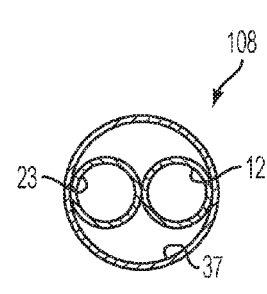
Figure 5I:
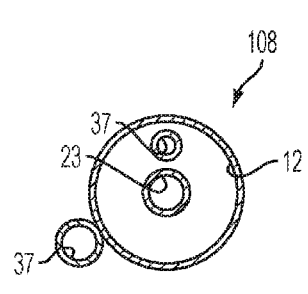
Figure 5J:
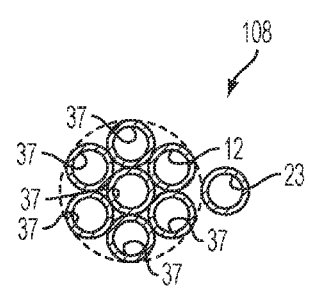

FIG. 4C provides an enlarged partial view of the catheter provided in FIG. 4B. In particular, at least one emitter 20 and at least one detector 22 are in electromagnetic radiation communication with one another, for example as illustrated by the radiation paths 24, wherein the electromagnetic radiation communication allows visible radiation or near infrared radiation emitted by the emitters 20 to be detected by one of the detectors 22 to determine tissue oxygenation of the region of the subject.

Alternatively, the catheter device 108 (or other types of interface members) may be used for, but not limited thereto, measuring the oxidation state (including, for example but not limited thereto, hemoglobin oxidation state) of a variety of anatomy locations of the subject besides the heart. For instance, the catheter device 108 (or other types of interface members) may be used for, but not limited thereto, measuring the oxidation state a variety of intended targets, such as organs, muscles, and blood. Still yet, the catheter device 108 (or other types of interface members) may be used for, but not limited thereto, measuring the oxidation state of a variety of regions such as, but not limited thereto, thoracic region, abdominal region, and pelvic region, as well as limbs, skull region and brain.

FIG. 5 provides various exemplary embodiments of the present invention interface member that may be implemented with the present invention oxidation measurement system. For instance, FIG. 5 provides a schematic exemplary cross-sectional view of various embodiments of the interface member that in the instant illustration is a catheter device 108 (or the like) having a lumen 12, as well as a secondary lumen 23, or any ancillary lumens 37 for that matter. Any of the lumens may be used for carrying the cardioplegia solution as well as the wire for transmitting the electromagnetic radiation, such as for an infrared spectroscopy system or device.

FIG. 5 depicts an aspect of various embodiments of the present invention that may provide a catheter system for delivering a cardioplegia material, diagnostic agent (not shown), therapeutic agent, or other medium to a site in the heart of a subject (or other anatomy of interest or other target or site) for treating or diagnosing at least a portion of the heart site (as shown in FIGS. 2-4, for example), and while using available medical imaging systems. FIGS. 5A-5J provide a schematic view of a representative cross-section of a catheter device 108 that may be taken at its distal catheter region, for example. As illustrated the catheter device may include a first lumen 12, second lumen 22, and a variety of ancillary lumens 37. The lumens may be any channel, passage, chamber, or conduit to transfer the requisite medium(s). FIGS. 5F and 5J depict lumens that are not necessarily contained in an enclosed structure per se but rather may assembled, associated or connected together to the extent necessary or desired to carry out the various techniques and systems of the present invention.

An aspect of an embodiment of the present invention device and method is that it will allow cardiac surgeons, cardiac anesthesiologists, and clinical perfusionists to assess the adequacy of cardioplegia/myocardial protection with no additional risk to the patient and with no additional procedural time.

Moreover, no currently existing coronary sinus catheters employ any technology designed to measure the oxygenation status of the myocardium. Additionally, existing coronary sinus catheters are unable to measure the oxygenation status of the myocardium. Cardiac surgeons therefore rely on imperfect strategies for the assessment of myocardial protection.

According to the CDC, approximately 415,000 patients undergo coronary artery bypass grafting in the United States per year (http://www.cdc.gov/nchs/fastats/insurg.htm). All of these patients, as well as those undergoing valve repair or replacement, could potentially benefit from the present invention technology.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

To a coronary sinus catheter, for instance, the following are affixed:

a) Two or more emitters of near infrared electromagnetic radiation, at least one of which must be below the isobestic point (800 nm) and at least one of which must be above the isobestic point, and b) Four or more detectors of near infrared electromagnetic radiation (photodiodes), at least two for each wavelength, spaced at known distances from the light source.

NIR radiation is emitted by all light sources and detected at the photodiodes. Assuming 750 and 850 nm are used for the high and low frequency wavelengths, respectively, tissue oxygenation ($StO_2$) can be described generally as:

$$StO_2 = f(\text{high frequency}_{near}, \text{high frequency}_{far}, \text{low frequency}_{near}, \text{low frequency}_{far})$$

$$StO_2 = f(850_{near}, 850_{far}, 750_{near}, 750_{far}).$$

The function used to estimate $StO_2$ can either be derived based on the Beer-Lambert law (which will produce a relative value for tissue oxygenation), or derived empirically (requires calibration of the device with tissue samples of known oxygen content).

To ensure contact between the NIR emitters and detectors and the left ventricle, the emitters and detectors can be mounted on an inflatable balloon. To ensure that the NIR radiation is directed into the myocardium, an array of multiple emitters and detectors can be utilize, and the pair with the highest signal strength selected for analysis.

Example and Experimental Results Set No. 2

Methods
Regulatory and Consent

This study was approved by the Institutional Review Board for Health Sciences Research at the University of Virginia (HSR16349) and was registered at the National Institutes of Health ClinicalTrials.gov registry (NCT01746576) prior to the commencement of data collection.

Twenty healthy adult (18-65 years of ge) volunteers were recruited to take part in this study. Because the Food and Drug Administration (FDA) considers dilated cardiomyopathy, congestive heart failure, pulmonary hypertension, aortic stenosis, flail chest, chest pain and shortness of breath contraindications to the use of the ResQGard (Advanced Circulatory Systems, Roseville, Minn.) impedance threshold device (ITD), these were the only exclusion criteria for this study. Informed written consent was obtained from all twenty volunteers.

Near Infrared Spectroscopy Device

A portable NIRS device was constructed by Artinis Medical Systems (Zetten, Netherlands), based on the PortaLite platform. The PortaLite devices utilizes light-emitting diodes (LEDs) of customizable wavelengths and a single receiving photodiode. Four LEDs of two standard wavelengths (759 and 840 nm) were utilized, both separated by 5 mm.

Data Acquisition

Subjects were positioned supine and a Nonin Model 8000AA transmittance pulse oximeter (connected to the OEM III board) was placed on the left index finger, a non-invasive blood pressure cuff was placed on the right arm and connected to a GE portable monitor (General Electric, Fairfield, Conn.), and an Advanced Circulatory Systems facemask was applied to the mouth using an elastic strap. The PortaLite NIRS device was applied to the left forehead and covered with an opaque drape. Both the PortaLite and OEM III transmitted data in real time to Windows-based laptop computers.

The ResQGard impedance threshold device was not applied initially. Blood pressure was measured, after which all external light sources were removed and recording from both pulse oximeter and NIRS device commenced. After five minutes of recording, the ITD was applied and two additional minutes of data were recorded. At the completion of data recording (7 minutes) but prior to removal of the ITD, blood pressure was re-measured.

Data Processing

The absorbance waveforms of red and infrared electromagnetic radiation from the pulse oximeter were available at 75 Hz temporal resolution. Using custom software written by the inventors (DAC and RHT) in MATLAB (The Mathwords, Natick, Mass.), the absorbance waveforms were transformed into the frequency domain using Fourier techniques. The spectral power at the respiratory (0.1-0.35) and cardiac (0.75-1.75 Hz) frequencies was calculated, and the spectral power ratio was calculated as previously described.

The PortaLite NIRS device exports the intensity (I) of detected electromagnetic radiation, which can be converted to optical density (OD) in accordance with the following equation:

$$OD = \log_{10}(I_0/I)$$

where $I_0$ represents the intensity of incident radiation (measured and provided by the manufacturer). Due to potential changes in LED wavelengths during diode warming, the first thirty seconds of data were discarded, in accordance with the manufacturer's recommendations.

In order to specifically analyze cerebral tissue, spatially resolved spectroscopy (SRS) techniques were utilized. Specifically, the difference in absorbance ($-\log_{10}[I/I_0]$) at two points was divided by the difference in absorbance by the optode spacing distance (5 mm). These spatially-resolved absorbance waveforms were utilized for the measurement of the relative concentration of various chromophores. Absorbance of electromagnetic radiation is related to the concentration of a chromophore in accordance with the Beer-Lambert law, which states:

$$A = \varepsilon c L$$

where $\varepsilon$ represents the absorption coefficient of an individual chromophore, c represents the concentration of each chromophore, and L represents path-length. We utilized Wray et al.'s data to estimate $\varepsilon$ (in $mM^{-1} \cdot cm^{-1}$). Because L and $\varepsilon$ are constant, relative changes in concentration can be estimated from relative changes in A (or I, since $I_0$ is known). Absolute measures of chromophore concentration require more sophisticated techniques such as phase modulation spectroscopy (PMS), which are not available on the PortaLite platform. The spatially-resolved absorbance waveforms were transformed into the frequency domain (as described above).

In order to estimate the relative concentration of two chromophores (Hgb, $HgbO_2$), the absorptivity of each chromophore at both wavelengths was extracted from Wray et al.'s dataset (because the frequency resolution of this dataset was on the order of 2-3 nm, linear interpolation was utilized as needed). The ultimate goal was to develop the following set of equations:

$$Hgb = x_{11}[A_{759}] + x_{12}[A_{8-10}]$$

$$HgbO_2 = x_{21}[A_{759}] + x_{22}[A_{840}]$$

Since the following is known:

$$A_{759} = \varepsilon_{Hgb,759}[Hgb] + \varepsilon_{Hgb\text{-}O2,759}[HgbO_2]$$

$$A_{840} = \varepsilon_{Hgb,840}[Hgb] + \varepsilon_{Hgb\text{-}O2,840}[HgbO_2]$$

$x_{1\text{-}2,1\text{-}2}$ can be determined by inverting the following matrix of absorption coefficients ($\varepsilon$):

|        | Hgb   | $HgbO_2$ |
|--------|-------|----------|
| 759 nm | 1.67  | 0.645    |
| 840 nm | 0.777 | 1.06     | the exact solution of which is leads to the following two equations:

$$Hgb \text{ (relative)} = 0.834 (A_{759}) - 0.509(A_{840})$$

$$HgbO_2 \text{ (relative)} = -0.613 (A_{759}) + 1.32(A_{840})$$

Data Analysis

The above matrix was utilized to calculate relative chromophore concentrations using seven algorithms (Table 1): baseline absorbance (0 Hz in the frequency domain), low frequency spectral peak (0.1-0.35 Hz), low frequency spectral power (0.1-0.35 Hz), high frequency spectral peak (0.75-1.75 Hz), and high frequency spectral power (0.75-1.75 Hz), total pulsatile peak (0.10-0.35 Hz+0.75-1.75 Hz), and total pulsatile power (0.10-0.35 Hz+0.75-1.75 Hz).

Because the path length of NIR radiation was unknown, relative chromophore concentrations could be estimated but absolute chromophore concentrations could not be measured. Thus, no comparisons of $StO_2$ between individuals were made. Rather, each individual served as his/her own control, and $StO_2$ estimations from algorithms 2-7 were compared to non-pulsatile $StO_2$ (algorithm 1).

For all available data points, we compared the calculated oxygen saturation at the low and high frequencies using both spectral peak and spectral power algorithms. Because data independence could not be assumed, pre- and post-ITD datasets were analyzed separately.

To determine the effect of respiratory impedance on the NIRS waveforms, spectral peak and power ratios for the spatially-resolved absorbance waveforms (average of all wavelengths) were calculated before and after the institution of restricted ventilation and compared to their PPG-derived analogues.

The statistical significance of all paired comparisons was assessed using the paired Student's t-test or the Wilcoxon signed-rank test, as appropriate, after testing for normality with the Kolmogorov-Smirnov test. Correlations were developed using the Pearson or Spearman correlation coefficients, as appropriate. Statistical significance was defined as a less than 5% probability of making a type I statistical error after conservatively correcting for multiple comparisons using the Bonferroni method.

Results

Twenty volunteers completed the study. Mean arterial blood pressure decreased by a median 3.5 mm Hg over the course of the study (p=0.0262, Wilcoxon signed rank test). $SpO_2$ averaged 97.9% before initiation of the ITD and 98.0% afterwards (p=0.425, paired t-test). There were no complications associated with ITD use.

Figure 6:
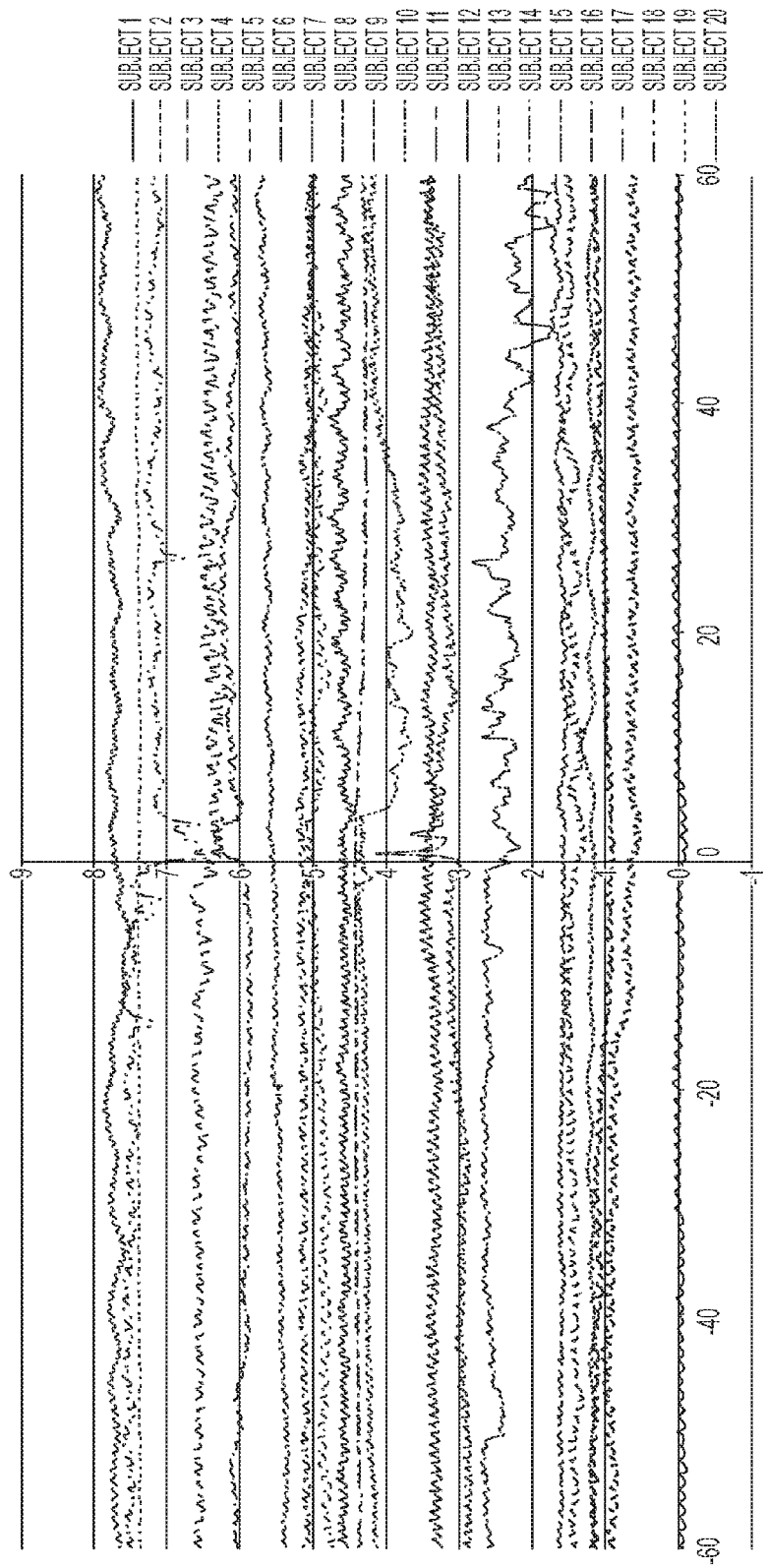
FIG. 6 graphically provides 840 nm NIRS waveforms for 30 seconds before and after initiation of the ITD for all subjects (scaled for visibility).

Pulsatile signal strength was weak. Relative to non-pulsatile absorbance, signal peak and power at low (0.1-0.35 Hz) and high (0.75-1.75) frequencies was 0.13, 1.3, 0.084, and 2.2%, respectively. Proximal (30 mm distance) 759 nm NIRS signals for all subjects for the 60 seconds before and after initiation of the ITD are displayed graphically in FIG. 6.

Figure 7:
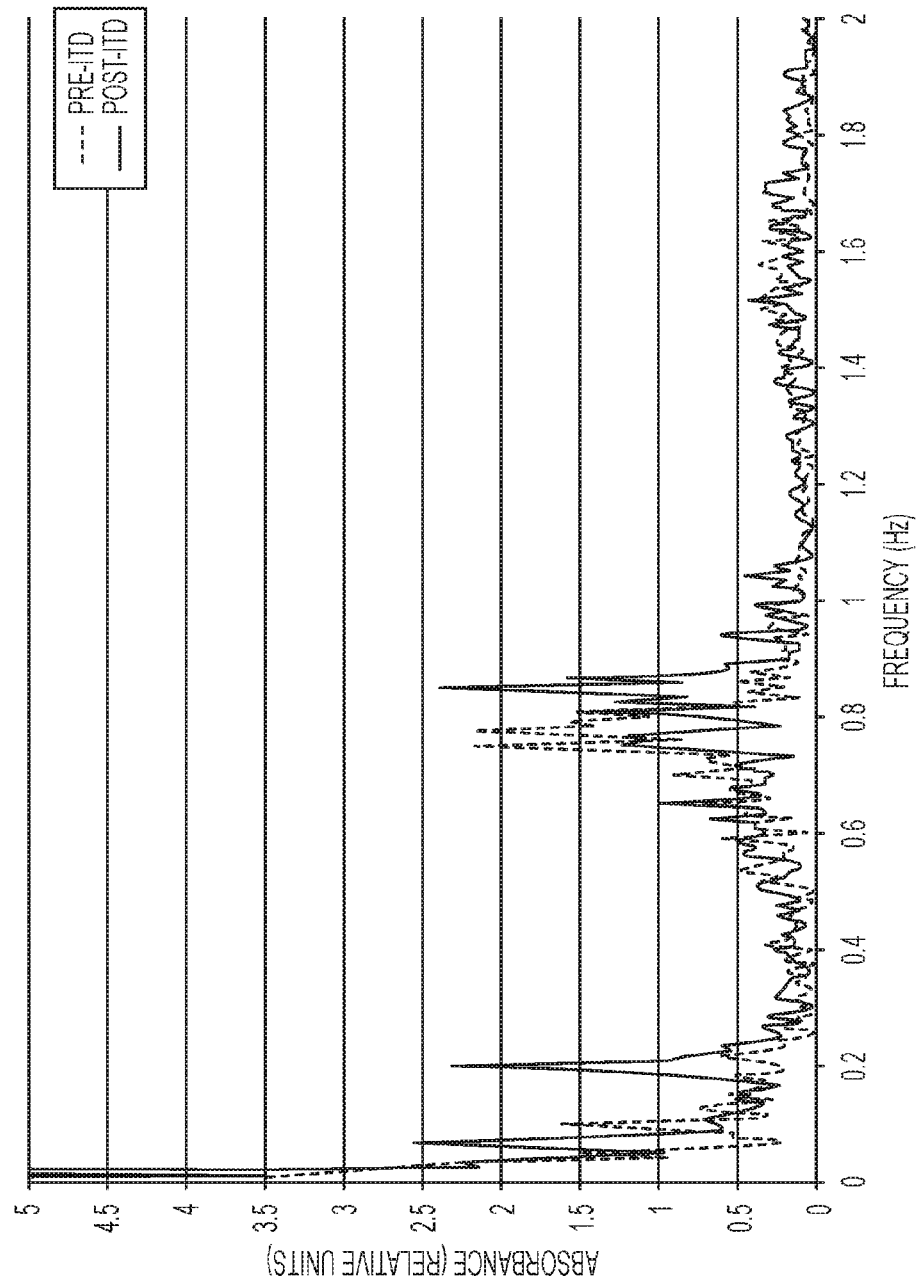
FIG. 7 graphically provides a frequency domain representation of 840 nm NIRS waveforms before and after initiation of the ITD, demonstrating an increase in the spectral peak associated with spontaneous ventilation.

Application of the ITD led to a statistically-significant, median 3.6% increase in non-pulsatile $StO_2$ (p=$5.2 \times 10^{-4}$, Wilcoxon signed rank test). The difference between pulsatile $StO_2$ and non-pulsatile $StO_2$ for all subjects is presented graphically in FIG. 7 and is summarized in Table 2. After taking into account multiple comparisons, only algorithm 4 (spectral peak ratio, 0.75-1.75 Hz) differed significant from the non-pulsatile algorithm (median increase 24%, p=0.0013, Wilcoxon signed rank test). The effect of respiratory impedance on $StO_2$ estimated by the pulsatile algorithms is presented in Table 3. Respiratory impedance did not lead to significant changes in any of the pulsatile algorithms (Wilcoxon signed rank test).

Figure 8:
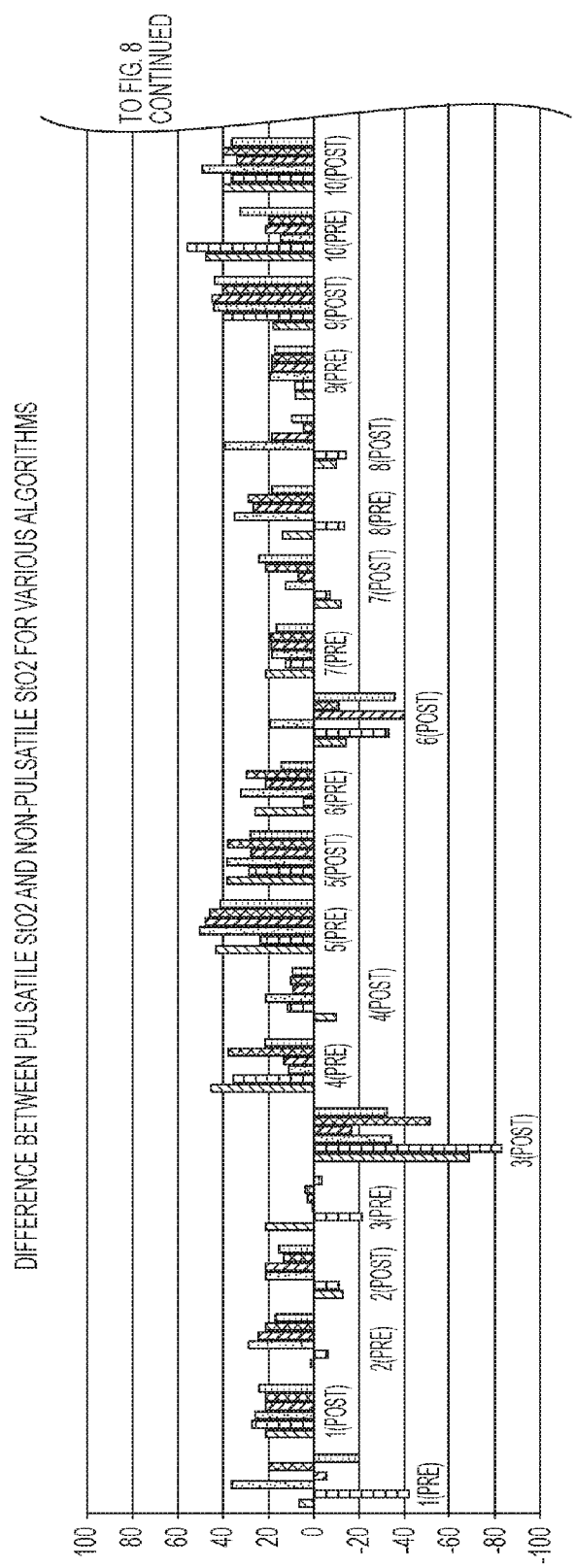
FIG. 8 graphically provides pulsatile estimates of $StO_2$ relative to non-pulsatile $StO_2$ for all subjects.
Figure 8:
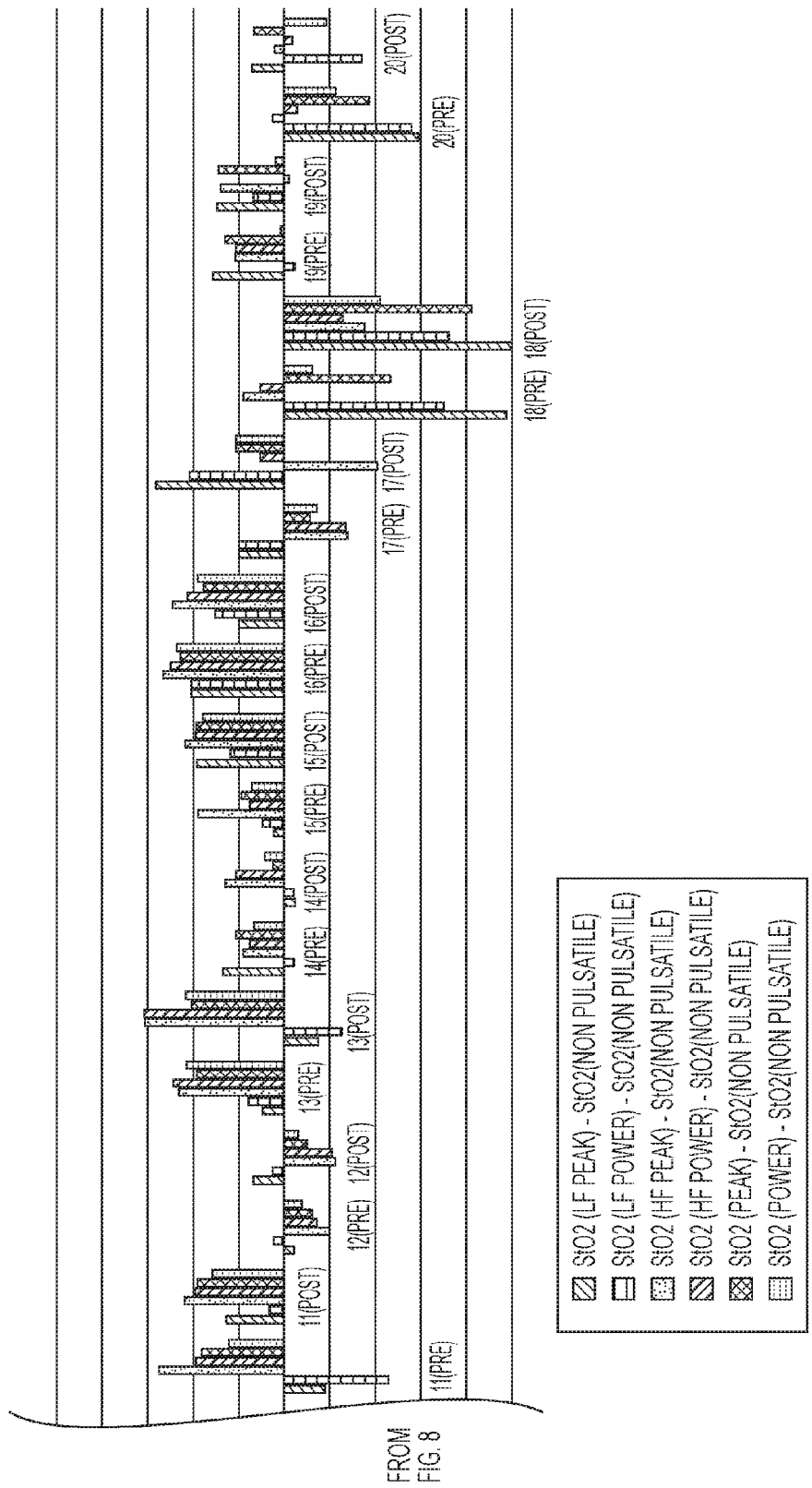
Figure 9:
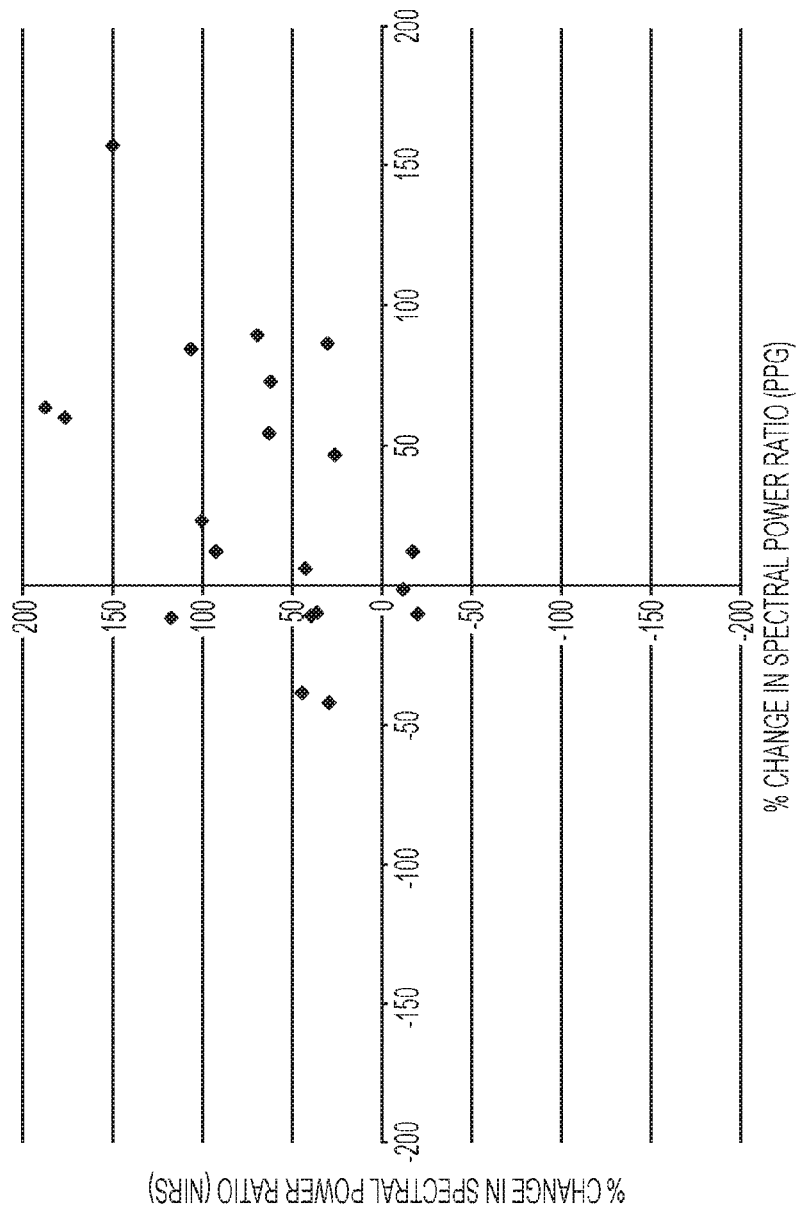
FIG. 9 graphically provides change in spectral power ratio in the pulse oximetry waveform as compared to change in spectral power ratio in the NIRS waveforms after initiation of the ITD.

The Spearman correlation coefficients describing the relationship between respiratory variation in the near infrared signals from the pulse oximeter and cerebral oximeter were −0.0690 and −0.155 for spectral peak ratio and spectral power, respectively. The Spearman correlation coefficients describing the relationship between changes in respiratory variation before and after initiation of the ITD were 0.0010 and 0.432 for spectral peak ratio and spectral power, respectively. Changes in spectral power ratio for the PPG and NIRS signals are displayed graphically in FIG. 8.

Discussion

Our results demonstrate, but not limited thereto, four significant findings—first, application of the ResQGard impedance threshold device in supine, healthy volunteers leads to a 3.5% increase in cerebral saturation as measured using traditional, non-pulsatile, spatially-resolved NIRS. Second, frequency domain analysis of NIRS signals at the respiratory and cardiac frequencies suggests that low and high frequency modulations in these signals cannot be exclusively attributed to venous and arterial blood, respectively; third, specific analysis of all pulsatile information occurring at the respiratory and cardiac frequencies leads to estimates of $StO_2$ that differ from non-pulsatile estimates of $StO_2$; fourth, while there is no meaningful correlation between respiratory variation in PPG and NIRS signals, changes in the spectral power ratio of NIRS appear to be correlated with changes in the spectral power ratio of PPG signals after application of an impedance threshold device.

Regarding the first claim—inventors suspected the mechanisms by which the ITD might increase cerebral $StO_2$ are through an increase in cardiac output (which has been demonstrated in multiple environments) or by decreasing the amount of venous blood in the cerebral vasculature. In animal models the ITD has been demonstrated to both lower right atrial and intracranial pressure, while increasing mean arterial pressure (the end result of which is increased cerebral perfusion). In our study, mean arterial pressure did not change. We suspect this is more likely due to a change in sympathetic tone which occurs after 7 minutes of supine rest and is not a reflection of the ITD's impact on hemodynamics. A third possibility for this increase is the potential effect of cerebral blood flow oscillation on cerebral hemodynamics. The ITD has been shown to prevent symptoms of cardiovascular collapse even when Doppler-based assessments of cerebral blood flow velocity are unchanged. Interestingly, the pulsatile component of cerebral blood flow is affected and it is believed that this may be protective.

Regarding the second claim—multiple authors have attempted to separate arterial and venous components of the PPG waveform using frequency domain analysis. This strategy has not, as of yet, led to the development of a device suitable for clinical use. Franceschini et al. specifically analyzed low frequency oscillations in NIRS waveforms from pigs subjected to hypoxia but did not assess high frequency oscillations. Importantly, these approaches all share the assumption that low frequency oscillations are exclusively due to oscillations in venous blood and that high frequency oscillations are exclusively due to oscillations in arterial blood. Were this the case, we would expect all of our low frequency estimates of $StO_2$ to be lower, and all of our high frequency estimates of $StO_2$ to be higher than non-pulsatile $StO_2$. In reality this only occurred in 28% of measurements. In the majority of cases (68% of peak and 60% of power measurements), the high and low frequency estimates of $StO_2$ were either both higher or both lower than non-pulsatile $StO_2$, suggesting that they were interrogating the same vascular beds.

Inventors point out that low arterial blood pressure oscillates at both the respiratory and cardiac frequencies. This knowledge has led to the development of the "fluid responsiveness" concept, new end-points for goal-directed therapy, and has resulted in the development of several commercially available devices. Similarly, the peripheral venous waveform also contains both low and high frequency spectral information. The pulse oximeter waveform clearly contains both low and high frequency oscillations, but how much of each has yet to be determined. Most likely, the low and high frequency components of the PPG and NIRS waveforms both contain contributions from both arterial and venous blood, the relative amounts of which are not known.

Certain cerebral oximeters use spatially-resolved spectroscopy (SRS) techniques in an attempt to isolate absorption signals due to cerebral tissue. This technique is not perfect, and significant extra-cranial contamination has been demonstrated. Whether or not this contamination could be attenuated by exclusively analyzing the pulsatile component of the NIRS signals has not been determined, but deserves further exploration. In theory, since non-pulsatile capillary flow only makes up approximately 2-10% of cerebral blood volume, exclusive analysis of pulsatile waveforms at physiologic frequencies could provide a means of reducing both noise (which does not generally recur at the respiratory or cardiac frequencies) and contamination from non-pulsatile tissue, although it should be pointed out that this would not solve the problem of determining the venous:arterial ratio.

Lastly, while respiratory variation in the systemic arterial pressure and PPG waveforms have been utilized to estimate fluid responsiveness, NIRS waveforms, which also oscillate at the respiratory frequency, have not. Interestingly, the utility of respiratory variation in the pulse oximeter waveform is dependent on the amplitude of the waveform. Because cerebral blood flow is relatively preserved in the face of adrenergic stimulation, respiratory variation in NIRS waveforms may be a useful, non-invasive measure of fluid responsiveness in critically-ill patients.

Our particular study has several limitations. First, we did not measure intrathoracic pressure changes after application of the ITD. Measurement of true intrathoracic pressure changes would require esophageal pressure monitoring, although measurement of pressure from the mask itself would have provided a reasonable surrogate. The current iteration of the ResQGard ITD has been calibrated by the manufacturer such that the average pressure change required to ventilate through the device is −7 cm $H_2O$ but there is some variation (which is dependent on the quality of mask seal as well as the respiratory rate). Individual differences may explain some of the variation seen in FIG. 6.

Another limitation of this study is our utilization of a two LED-based device. As opposed to laser light sources, which offer a narrow band width, LEDs produce a range of frequencies, which can decrease their accuracy (that said, most commercially available devices use LEDs, not lasers). Additionally, the accuracy of NIRS devices appears to increase with the inclusion of additional wavelengths of NIR radiation, thus a 3 or 4 wavelength device may have produced more accurate results.

Lastly, because we did not utilize a device capable of estimating the path-length of NIR radiation, we were only able to estimate changes in chromophore concentrations, and not absolute values. This does not impact the comparisons within individuals but precluded comparisons between individuals.

Conclusions of Study

Application of an impedance threshold device to spontaneously ventilating healthy subjects increases measured non-pulsatile cerebral oxygen saturation. Specific analysis of oscillations in spatially-resolved NIRS signals at the respiratory and cardiac frequencies of healthy human volunteers before and after application of an impedance threshold device suggests that both spectra contain signals from arterial and venous blood, the relative amounts of which are not known. Estimates of $StO_2$ from NIR signals which oscillate at the respiratory and cardiac frequencies differ from non-pulsatile estimates of $StO_2$. NIRS spectral power ratio may offer a useful alternative to PPG-derived indices of fluid responsiveness in patients in whom peripheral perfusion is compromised.

TABLE 1

Summary of algorithms tested

| Algorithm Number | Frequency Range (Hz) | Technique | Comments |
|---|---|---|---|
| 1 | 0 | n/a | Analyzes only baseline absorbance (neglects any oscillations) |
| 2 | 0.10-0.35 | Spectral Peak | Chosen to specifically analyze respiration-induced oscillations |
| 3 | 0.10-0.35 | Spectral Power | Chosen to specifically analyze respiration-induced oscillations |
| 4 | 0.75-1.75 | Spectral Peak | Chosen to specifically analyze cardiac contraction-induced oscillations |
| 5 | 0.75-1.75 | Spectral Power | Chosen to specifically analyze cardiac contraction-induced oscillations |
| 6 | 0.10-0.35 + 0.75-1.75 | Spectral Peak | Chosen to specifically analyze any oscillation that occurs at either the respiratory or cardiac frequencies |
| 7 | 0.10-0.35 + 0.75-1.75 | Spectral Power | Chosen to specifically analyze any oscillation that occurs at either the respiratory or cardiac frequencies |

TABLE 2

Mean, median, STDEV, and statistical significance of the difference in estimated oxygen saturation for pulsatile algorithms (algorithms 2-7) as compared to non-pulsatile $StO_2$ (algorithm 1) before and after initiation of restricted ventilation. Additionally, the difference between estimated oxygen saturation measured at the high and low frequencies is compared for both the peak and power algorithms (algorithm 4-2, algorithm 5-3)

| | | Algorithm 2 | Algorithm 3 | Algorithm 4 | Algorithm 5 | Algorithm 6 | Algorithm 7 | Algorithm 4-2 | Algorithm 5-3 |
|---|---|---|---|---|---|---|---|---|---|
| Pre-ITD | Mean | 8.45 | −1.18 | 22.87 | 16.28 | 17.53 | 12.35 | 14.41 | 17.47 |
| | Median | 16.04 | 4.95 | 21.10 | 17.45 | 23.57 | 15.38 | 9.87 | 17.04 |
| | STDEV | 40.26 | 32.62 | 22.55 | 20.79 | 25.07 | 20.44 | 44.34 | 33.53 |
| | p-value | | | | | | | | |
| Post-ITD | Mean | 1.72 | −0.59 | 20.30 | 14.86 | 11.41 | 10.86 | 18.58 | 15.45 |
| | Median | 14.01 | 6.10 | 26.31 | 20.66 | 17.83 | 12.92 | 25.44 | 12.85 |
| | STDEV | 41.38 | 35.03 | 30.79 | 26.48 | 31.57 | 26.17 | 39.97 | 29.46 |
| | p-value | | | | | | | | |

TABLE 3

Effect of respiratory impedance on $StO_2$ estimates from all pulsatile algorithms.

| | | Algorithm 2 | Algorithm 3 | Algorithm 4 | Algorithm 5 | Algorithm 6 | Algorithm 7 |
|---|---|---|---|---|---|---|---|
| Post-Pre | Mean | −6.74 | 0.59 | −2.56 | −1.42 | −6.11 | −1.48 |
| | Median | −6.88 | −0.86 | −2.67 | −2.02 | −3.15 | −1.09 |

TABLE 3-continued

Effect of respiratory impedance on $StO_2$ estimates from all pulsatile algorithms.

| | | Algorithm 2 | Algorithm 3 | Algorithm 4 | Algorithm 5 | Algorithm 6 | Algorithm 7 |
|---|---|---|---|---|---|---|---|
| ITD | STDEV p-value | 37.32 | 31.13 | 19.69 | 22.73 | 26.27 | 22.40 |

ADDITIONAL EXAMPLES

Example 1

An aspect of an embodiment of the present invention provides, but not limited thereto, a system for measuring the oxidation state of biological molecules in a region of a measurement site of a subject. The system may comprise: at least one emitter configured to be in optical communication with the region of the measurement site of the subject; at least one detector configured to be in optical communication with the region of the measurement site of the subject; wherein the at least one emitter or the at least one detector is configured to be disposed inside the subject; and the at least one emitter and the at least one detector are in electromagnetic radiation communication with one another, wherein the electromagnetic radiation communication allows visible radiation or near infrared radiation emitted by the at least one emitters to be detected by the at least one detector to determine tissue oxidation state of the region of the measurement site of the subject.

Example 2

The system of example 1, wherein both said at least one emitter and said at least one detector are configured to be disposed inside the subject.

Example 3

The system of example 1, further comprising:
an interface member, wherein at least a portion of said system is in mechanical communication with said interface member.

Example 4

The system of example 3, wherein said interface member includes a device that includes a proximal region a distal regional, and a longitudinal region there between.

Example 5

The system of example 4, further comprising an expandable component in mechanical communication with said interface member distal region, and located between said at least one emitter and said at least one detector and said interface member distal region.

Example 6

The system of example 5, wherein said expandable component is configured to assure that said at least one emitter and said at least one detector makes contact with tissue wall of the subject.

Example 7

The system of example 5, wherein said expandable component includes at least one of the following: a balloon, expandable structure, stent, smart memory alloy (SMA) device, or inflatable compartment.

Example 8

The system of example 3, further comprises an electromagnetic radiation source in communication with said at least one detector.

Example 9

The system of example 8, wherein said electromagnetic radiation source and said at least one emitter and said at least one detector comprises a visible-infrared or near-infrared spectroscopic system, or both a visible-infrared or near-infrared spectroscopic system.

Example 10

The system of example 3, wherein said at least one emitter and said at least one detector is in communication with a processor.

Example 11

The system of example 3, further comprising at least one port 13 in communication with said interface member.

Example 12

The system of example 11, wherein said at least one port is configured for delivering cardioplegia solution.

Example 13

The system of example 3, wherein said interface member includes a distal tip 10, wherein said system further comprising at least one port disposed on said distal tip.

Example 14

The system of example 13, wherein said at least one port is configured for delivering cardioplegia solution.

Example 15

The system of example 1, comprising:
an interface member, wherein said at least one emitter is in mechanical communication with said interface member.

Example 16

The system of example 1, comprising:
an interface member, wherein said at least one detector is in mechanical communication with said interface member.

Example 17

The system of example 1, comprising:
an interface member, wherein said at least one emitter and said at least one detector are in mechanical communication with said interface member.

Example 18

The system of any one of examples 15, 16 or 17, wherein said interface member comprises a medical device.

Example 19

The system of example 18, wherein said medical device comprises a diagnostic or therapeutic device.

Example 20

The system of example 19, wherein said diagnostic device comprises a surgical device or a monitoring device.

Example 21

The system of example 18, wherein said medical device comprises a catheter.

Example 22

The system of example 18, wherein said medical device comprises at least one of the following: a substrate, probe, patch, drain, guidewire, tube, drainage tube, conduit, elongated member, lumen, circuit board, encapsulant, casing, packaging, housing, or membrane.

Example 23

The system of example 18, wherein said medical device comprise an ultrasound device.

Example 24

The system of example 1, wherein said at least one emitter being configured to make contact with the measurement site.

Example 25

The system of example 1, wherein said at least one detector being configured to make contact with the measurement site.

Example 26

The system of example 1, wherein said at least one emitter and said at least one detector are configured to make contact with the measurement site.

Example 27

The method of example 1, wherein the device is configured to measure the oxidation state of biological molecules that includes hemoglobin of blood.

Example 28

The method of example 1, wherein the device is configured to measure the oxidation state of biological molecules that includes at least one of myoglobin or cytochrome of the muscle or heart.

Example 29

The method of example 1, wherein the device is configured to measure the oxidation state of biological molecules that includes at least one of Hemoglobin or cytochrome of the heart.

Example 30

The method of example 1, wherein the device is configured to measure the oxidation state of biological molecules that includes at least one of Hemoglobin or cytochrome of an organ.

Example 31

The system of example 18, further comprising:
an expandable component in mechanical communication with said medical device.

Example 32

The system of example 31, wherein said expandable component is configured to assure that said at least one emitter and said at least one detector makes contact with tissue wall of the subject.

Example 33

The system of example 31, wherein said expandable component includes at least one of the following: a balloon, expandable structure, stent, smart memory alloy (SMA) device, or inflatable compartment.

Example 34

The system of example 1, further comprises an electromagnetic radiation source in communication with said at least one detector.

Example 35

The system of example 34, wherein said electromagnetic radiation source and said at least one emitter and said at least one detector comprises a visible-infrared or near-infrared spectroscopic system, or both a visible-infrared or near-infrared spectroscopic system.

Example 36

The system of example 1, wherein:
said at least one emitter comprises a light emitting diode (LED); and
said at least one detector comprises photo detector.

Example 37

The system of example 1, wherein said at least one emitter and said at least one detector is in communication with a processor.

Example 38

The system of example 37, wherein said processor is configured to perform the algorithmic steps to determine the tissue oxygenation ($StO_2$) of the region of the subject.

Example 39

The system of example 38, wherein said tissue oxygenation ($StO_2$) of the region of the subject is accomplished using Bee-Lambert law or empirical derivation.

Example 40

The system of example 18, further comprising at least one port 13 in communication with said medical device.

Example 41

The system of example 40, wherein said at least one port is configured for delivering cardioplegia solution.

Example 42

The system of example 18, wherein said medical device includes a distal tip 10, wherein said system further comprising at least one port disposed on said distal tip.

Example 43

The system of example 42, wherein said at least one port is configured for delivering cardioplegia solution.

Example 44

The system of example 3, comprising:
at least two of said emitters; wherein one of said emitters is configured to emit the electromagnetic radiation at a high frequency so as to be above an isobestic point and one of said emitters is configured to emit the electromagnetic radiation at a low frequency so as to below the isobestic point; and
at least four of said detectors; said four detectors located in communication with said interface member so as to be at a known predetermined distance from respective said at least two emitters, whereby two of said detectors are provided for each of the referenced high and low frequencies of said emitters.

Example 45

The system of example 44, wherein said at least two emitters and said at least four detectors are in communication with a processor.

Example 46

The system of example 45, wherein said processor is configured to perform the algorithmic steps to determine the tissue oxygenation ($StO_2$) of the region of the subject.

Example 47

The system of example 46, wherein the tissue oxygenation ($StO_2$) is determined by the execution of the following formula:

$$StO_2 = f(\text{high frequency}_{near}, \text{high frequency}_{far}, \text{low frequency}_{near}, \text{low frequency}_{far})$$

Example 48

The system of example 1, wherein said region is myocardium.

Example 49

The system of example 48, wherein said myocardium is located in the left ventricle of the heart.

Example 50

An aspect of an embodiment of the present invention provides, but not limited thereto, a catheter system for measuring the oxidation state of biological molecules in a region of a measurement site of a subject. The system may comprise: a catheter device having a lumen, the catheter device includes proximal region, a distal regional, and a longitudinal region there between; at least one emitter in mechanical communication with the catheter distal region and configured to make contact with a tissue wall of the subject; at least one detector in mechanical communication with the catheter distal region and configured to make contact with the tissue wall of the subject; and the at least one emitter and the at least one detector are in electromagnetic radiation communication with one another, wherein the electromagnetic radiation communication allows visible radiation or near infrared radiation emitted by the at least one emitters to be detected by the at least one detector to determine tissue oxidation state of the region of the measurement site of the subject.

Example 51

The system of example 50, further comprising:
an expandable component in mechanical communication with said catheter distal region, and located between said at least one emitter and said at least one detector and said catheter distal region.

Example 52

The system of example 51, wherein said expandable component is configured to assure that said at least one emitter and said at least one detector makes contact with the tissue wall.

Example 53

The system of example 51, wherein said expandable component includes at least one of the following: a balloon, expandable structure, stent, smart memory alloy (SMA) device, or inflatable compartment.

Example 54

The system of example 50, wherein the region of the measurement site is myocardium.

Example 55

The system of example 50, wherein the region of the measurement site is at least one of the following: blood, tissue, muscle, or organ.

Example 56

An aspect of an embodiment of the present invention provides, but not limited thereto, a method for measuring the oxidation state of biological molecules in a region of a measurement site of a subject. The method may comprise: providing at least one emitter in optical communication with the region of the measurement site of the subject; providing at least one detector in optical communication with the region of the measurement site of the subject; disposing the at least one emitter or the at least one detector inside the subject; and communicating electromagnetic radiation between the at least one emitter and the at least one detector, wherein the electromagnetic radiation communication allows visible radiation or near infrared radiation emitted by the at least one emitters to be detected by the at least one detector to determine tissue oxidation state of the region of the measurement site of the subject.

Example 57

The method of example 56, comprising:
disposing both said at least one emitter and said at least one detector inside the subject.

Example 58

The method of example 56, further comprising:
providing an interface member, wherein:
said at least one emitter or said at least one detector is in mechanical communication with said an interface member; or
both said at least one emitter and said at least one detector are in mechanical communication with said an interface member.

Example 59

The method of example 58, further comprising:
providing an expandable component in mechanical communication with said interface member.

Example 60

The method of example 59, wherein said expandable component is configured to assure that said at least one emitter and said at least one detector makes contact with tissue wall of the subject.

Example 61

The method of example 59, wherein said expandable component includes at least one of the following: a balloon, expandable structure, stent, smart memory alloy (SMA) device, or inflatable compartment.

Example 62

The method of example 56, further comprises providing an electromagnetic radiation source in communication with said at least one detector.

Example 63

The method of example 62, wherein said electromagnetic radiation source and said at least one emitter and said at least one detector comprises a visible-infrared or near-infrared spectroscopic system, or both a visible-infrared or near-infrared spectroscopic system.

Example 64

The method of example 56, further comprising communicating said at least one emitter and said at least one detector is with a processor.

Example 65

The method of example 58, further comprising at least one port in communication with said interface member.

Example 66

The method of example 65, wherein said at least one port is configured for delivering cardioplegia solution.

Example 67

The method of example 58, wherein said interface member includes a distal tip, wherein said system further comprising at least one port disposed on said distal tip.

Example 68

The system of example 67, wherein said at least one port is configured for delivering cardioplegia solution.

Example 69

The method of example 56, comprising:
providing an interface member in mechanical communication with said at least one emitter.

Example 70

The method of example 56, comprising:
providing an interface member in mechanical communication with said at least one detector.

Example 71

The method of example 56, comprising:
providing an interface member in mechanical communication with said at least one emitter and said at least one detector.

Example 72

The method of any one of examples 69, 70 or 71, wherein said interface member comprises a medical device.

Example 73

The method of example 72, wherein said medical device comprises a diagnostic or therapeutic device.

Example 74

The method of example 73, wherein said diagnostic device comprises a surgical device or a monitoring device.

Example 75

The method of example 72, wherein said medical device comprises a catheter.

Example 76

The method of example 72, wherein said medical device comprises at least one of the following: a substrate, probe, patch, drain, guidewire, tube, drainage tube, conduit, elongated member, lumen, circuit board, encapsulant, casing, packaging, housing, or membrane.

Example 77

The method of example 72, wherein said medical device comprise an ultrasound device.

Example 78

The method of example 64, further comprising:
perform algorithmic steps using said processor to determine the tissue oxygenation ($StO_2$) of the region of the subject.

Example 79

The method of example 78, wherein said tissue oxygenation ($StO_2$) of the region of the subject is accomplished using Bee-Lambert law or empirical derivation.

Example 80

An aspect of an embodiment of the present invention provides, but not limited thereto, a method for measuring the oxidation state of biological molecules in a region of a measurement site of a subject. The method may comprise: providing a catheter device having a lumen, the catheter device includes proximal region, a distal regional, and a longitudinal region there between; providing at least one emitter configured to make contact with a tissue wall of the subject; providing at least one detector configured to make contact with the tissue wall of the subject; and communicating electromagnetic radiation between the at least one emitter and the at least one detector, wherein the electromagnetic radiation communication allows visible radiation or near infrared radiation emitted by the at least one emitters to be detected by the at least one detector to determine tissue oxidation state of the region of the measurement site of the subject.

Example 81

The method of example 80, further comprising:
providing an expandable component in mechanical communication with said catheter distal region, and located between said at least one emitter and said at least one detector and said catheter distal region.

Example 82

The method of example 81, further comprising:
engaging said expandable component to assure that said at least one emitter and said at least one detector makes contact with the tissue wall.

Example 83

The method of example 64, further comprising:
performing algorithmic steps using said processor to determine the tissue oxygenation ($StO_2$) of the region of the subject.

Example 84

The method of example 83, wherein said tissue oxygenation ($StO_2$) of the region of the subject is accomplished using Bee-Lambert law or empirical derivation.

Example 85

The method of example 80, comprising:
providing at least two of said emitters; wherein one of said emitters is configured to emit the electromagnetic radiation at a high frequency so as to be above an isobestic point and one of said emitters is configured to emit the electromagnetic radiation at a low frequency so as to below the isobestic point; and
providing at least four of said detectors; said four detectors located in communication with said catheter distal region so as to be at a know predetermined distance from respective said at least two emitters, whereby two of said detectors are provided for each of the referenced high and low frequencies of said emitters.

Example 86

The method of example 85, wherein said at least two emitters and said at least four detectors are in communication with a processor.

Example 87

The method of example 86, wherein said processor is configured to perform the algorithmic steps to determine the tissue oxygenation ($StO_2$) of the region of the subject.

Example 88

The method of example 87, wherein the tissue oxygenation ($StO_2$) is determined by the execution of the following formula:

$$StO_2 = f(\text{high frequency}_{near}, \text{high frequency}_{far}, \text{low frequency}_{near}, \text{low frequency}_{far})$$

Example 89

The method of example 80, wherein said region is myocardium.

Example 90

The method of manufacturing any of the systems, devices or subject matter disclosed in one or more of any combination of examples 1-55).

Example 91

The method of using any of the systems, devices, or subject matter disclosed in one or more of any combination of examples 1-55).

Example 92

The method of manufacturing any of the systems, devices or subject matter disclosed in one or more of any combination of References 1-75 listed below).

Example 93

The method of using any of the systems, devices, or subject matter disclosed in one or more of any combination of References 1-75 listed below).

REFERENCES

The following patents, applications and publications as listed below and throughout this document are hereby incorporated by reference in their entirety herein. The devices, systems, compositions, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Application Publication Serial No. US 2011/0092951 A1, Vaisnys, et al., "Method and Apparatus for Cardiac Tissue Monitoring and Catheter-Based Perfusion for Mitigation Acute Reoxygenation Injury", Apr. 21, 2011.
2. U.S. Pat. No. 6,031,603, Filed Jul. 9, 1998—Issued Feb. 29, 2000—Ilya Fine—Cybro Medical, Ltd., "Sensor, method and device for optical blood oximetry."
3. U.S. Pat. No. 5,597,377, Filed May 6, 1994—Issued Jan. 28, 1997—Gabriel S. Aldea—Trustees of Boston University, "Coronary sinus reperfusion catheter."
4. U.S. Pat. No. 6,591,144, Filed Oct. 23, 2001—Issued Jul. 8, 2003—John D. Pigott—The Administrators of the Tulane Educational Fund, "Steerable catheter and method for locating coronary sinus."
5. U.S. Pat. No. 8,216,228, Filed Oct. 22, 2010—Issued Jul. 10, 2012—Jose Carlos Pachon Mateos—St. Jude Medical, Atrial Fibrillation Division, Inc., "Apparatus and methods for arrhythmia treatment based on spectral mapping during sinus rhythm."
6. WO 03/035139 A2, Pigott, J., "Steerable Catheter and Method for Locating Coronary Sinus", May 1, 2003.
7. U.S. Pat. No. 5,423,772, Lurie, et al., "Coronary Sinus Catheter", Jun. 13, 1995.
8. U.S. Patent Application Publication No. US 2009/0105605 A1, Abreu, M., "Apparatus and Method for Measuring Biologic Parameters", Apr. 23, 2009.
9. International Patent Application Publication No. WO 2007/050487 A2, Abreu, M., "Apparatus and Method for Measuring Biologic Parameters", May 3, 2007.
10. U.S. Patent Application Publication No. US 2005/0187488 A1, Wolf, E., "System for Transcutaneous Monitoring of Intracranial Pressure (ICP) Using Near Infrared (NIR) Telemetry", Aug. 25, 2005.
11. U.S. Pat. No. 7,435,229 B2, Wolf, E., "System for Transcutaneous Monitoring of Intracranial Pressure (ICP) Using Near Infrared (NIR) Telemetry", Oct. 14, 2008.
12. U.S. Pat. No. 5,995,208, Sarge, et al., "Intravascular Oximetry Catheter", Nov. 30, 1999.
13. European Patent Application Publication No. EP 1547 515 A1, Barts and The London National Health Service Trust, et al., "Optical fibre catheter pulse oximeter", Jun. 29, 2005.
14. U.S. Pat. No. 7,120,481 B2, Keller, et al., "Probe and Apparatus for Measuring Cerebral Hemodynamics and Oxygenation", Oct. 10, 2006.
15. International Patent Application No. WO 2005/060825 A1, Phillips, J., et al., "Optical Fibre Catheter Pulse Oximeter", Jul. 7, 2005.
16. International Patent Application No. WO 90/07907, Hariri, R., et al., "Infrared Oximetry Measuring Device", Jul. 26, 1990.
17. U.S. Pat. No. 8,073,517 B1, Burchman, C., "System and Method for Measuring Blood Constituents Using a Catheter", Dec. 6, 2011.
18. International Patent Application Serial No. PCT/US2013/060404, Elias, et al., "Method and System for Enhanced Imaging Visualization of Deep Brain Anatomy Using Infusion", filed Sep. 18, 2013.
19. U.S. patent application Ser. No. 13/704,782 entitled "METERS FOR IN-VIVO MONITORING," filed Jul. 30, 2013.
20. International Patent Application No. PCT/US2011/040976 entitled "METERS FOR IN-VIVO MONITORING," filed Jun. 17, 2011.
21. U.S. patent application Ser. No. 13/780,207 entitled "System and Method for Magnetic Control of an Anesthetic," filed Feb. 28, 2013.
22. U.S. patent application Ser. No. 13/607,993 entitled "Access Needle Pressure Sensor Device and Method of Use," filed Sep. 10, 2012; U.S. Patent Application Publication No. US-2012-0330184, Dec. 27, 2012.
23. U.S. patent application Ser. No. 12/530,830 entitled "Access Needle Pressure Sensor Device and Method of Use," filed Sep. 11, 2009.
24. International Patent Application No. PCT/US2008/056643 entitled "Access Needle Pressure Sensor Device and Method of Use," filed Mar. 12, 2008.
25. U.S. patent application Ser. No. 13/579,745 entitled "ACCESS SYSTEM FOR FEMORAL VASCULATURE CATHETERIZATION AND RELATED METHOD," filed Aug. 17, 2012.
26. International Patent Application No. PCT/US2010/061413 entitled "ACCESS SYSTEM FOR FEMORAL VASCULATURE CATHETERIZATION AND RELATED METHOD," filed Dec. 21, 2010.
27. U.S. patent application Ser. No. 13/579,882 entitled "SYSTEM, METHOD, AND COMPUTER PROGRAM PRODUCT FOR SIMULATING EPICARDIAL ELECTROPHYSIOLOGY PROCEDURES," filed Aug. 17, 2012.
28. International Patent Application No. PCT/US2011/025470 entitled "SYSTEM, METHOD, AND COMPUTER PROGRAM PRODUCT FOR SIMULATING EPICARDIAL ELECTROPHYSIOLOGY PROCEDURES," filed Feb. 18, 2011; U.S. Patent Application Publication No. WO 2011/103456, Aug. 25, 2011.
29. U.S. patent application Ser. No. 13/559,008 entitled "Blood Flow Bypass Catheters and Methods for the Delivery of Medium to the Vasculature and Body Ducts," filed Jul. 26, 2012.
30. U.S. patent application Ser. No. 12/625,153 entitled "Blood Flow Bypass Catheters and Methods for the Delivery of Medium to the Vasculature and Body Ducts," filed Nov. 24, 2009; U.S. Pat. No. 8,255,193, issued Aug. 28, 2012.
31. U.S. patent application Ser. No. 11/884,421 entitled "Blood Flow Bypass Catheters and Methods for the Delivery of Medium to the Vasculature and Body Ducts," filed Aug. 15, 2007.
32. International Patent Application No. US2006/005876 entitled "Blood Flow Bypass Catheters and Methods for the Delivery of Medium to the Vasculature and Body Ducts," filed Feb. 16, 2006.
33. U.S. patent application Ser. No. 13/540,348 entitled "Coaxial Catheter Systems for Transference of Medium,"

filed Jul. 2, 2012; U.S. Patent Application Publication No. 2013/0090556, Apr. 11, 2013.
34. U.S. patent application Ser. No. 12/760,837 entitled "Coaxial Catheter Systems for Transference of Medium," filed Apr. 15, 2010; U.S. Pat. No. 8,211,083, issued Jul. 3, 2012.
35. U.S. patent application Ser. No. 11/191,676 entitled "Coaxial Catheter Systems for Transference of Medium," filed Jul. 28, 2005; U.S. Pat. No. 7,727,225, issued Jun. 1, 2010.
36. International Patent Application No. PCT/US2005/026738 entitled "Coaxial Catheter Systems for Transference of Medium," filed Jul. 28, 2005.
37. U.S. patent application Ser. No. 13/464,762 entitled "SYSTEMS AND METHODS FOR DETERMINING LOCATION OF AN ACCESS NEEDLE IN A SUBJECT," filed May 4, 2012; U.S. Patent Application Publication No. US-2012-0283582-A1, Nov. 8, 2012. 20. U.S. patent application Ser. No. 13/464,752 entitled "SYSTEMS AND METHODS FOR DETERMINING LOCATION OF AN ACCESS NEEDLE IN A SUBJECT," filed May 4, 2012; U.S. Patent Application Publication No. US-2012-0310052-A1, Dec. 6, 2012.
38. U.S. patent application Ser. No. 13/318,450 entitled "ACCESS TROCAR AND RELATED METHOD THEREOF," filed Nov. 1, 2011.
39. International Patent Application No. PCT/US2010/033189 entitled "ACCESS TROCAR AND RELATED METHOD THEREOF," filed Apr. 30, 2010.
40. U.S. patent application Ser. No. 12/741,710 entitled "STEERABLE EPICARDIAL PACING CATHETER SYSTEM PLACED VIA THE SUBXIPHOID PROCESS," filed May 6, 2010; U.S. Patent Application Publication No. 2010/0241185, Sep. 23, 2010.
41. International Patent Application No. PCT/US2008/082835 entitled "STEERABLE EPICARDIAL PACING CATHETER SYSTEM PLACED VIA THE SUBXIPHOID PROCESS," filed Nov. 7, 2008.
42. U.S. patent application Ser. No. 12/513,258 entitled "Means and Methods for Cytometric Therapies," filed Mar. 17, 2010; U.S. Patent Application Publication No. 2010/0210927, Aug. 19, 2010.
43. International Patent Application No. PCT/US2007/023047 entitled "Means and Methods for Cytometric Therapies," filed Nov. 1, 2007.
44. International Patent Application No. US2006/005876 entitled "Blood Flow Bypass Catheters and Methods for the Delivery of Medium to the Vasculature and Body Ducts," filed Feb. 16, 2006.
45. U.S. patent application Ser. No. 12/532,233 entitled "Electrode Catheter for Ablation Purposes and Related Method Thereof," filed Sep. 21, 2009; U.S. Patent Application Publication No. 2010/0211064, Aug. 19, 2010.
46. International Patent Application No. PCT/US2008/057626 entitled "Electrode Catheter for Ablation Purposes and Related Method Thereof," filed Mar. 20, 2008.
47. U.S. patent application Ser. No. 12/530,938 entitled "Epicardial Ablation Catheter and Method of Use," filed Sep. 11, 2009; U.S. Patent Application Publication No. 2010/0114093, May 6, 2010.
48. International Patent Application No. PCT/US2008/056816 entitled "Epicardial Ablation Catheter and Method of Use," filed Mar. 13, 2008.
49. U.S. patent application Ser. No. 12/304,801 entitled "Closure Device for Skull Plates and Related Method Thereof," filed May 18, 2009; U.S. Pat. No. 8,226,694, issued Jul. 24, 2012.
50. International Patent Application No. PCT/US2007/014881 entitled "Closure Device for Skull Plates and Related Method Thereof," filed Jun. 26, 2007.
51. U.S. patent application Ser. No. 12/375,139 entitled "System and Method for Intracranial Implantation of Therapeutic or Diagnostic Agents," filed Jan. 27, 2009; U.S. Patent Application Publication No. 2009/0192487, Jul. 30, 2009.
52. International Patent Application No. PCT/US2007/016256 entitled "System and Method for Intracranial Implantation of Therapeutic or Diagnostic Agents," filed Jul. 18, 2007.
53. U.S. patent application Ser. No. 12/160,378 entitled "Multi-Port Catheter System with Medium Control and Measurement Systems for Therapy and Diagnosis Delivery," filed Aug. 1, 2008; U.S. Patent Application Publication No. 2009-0048577, Feb. 19, 2009.
54. International Patent Application No. PCT/US2007/000353 entitled "Multi-Port Catheter System with Medium Control and Measurement Systems for Therapy and Diagnosis Delivery," filed Jan. 9, 2007.
55. International Patent Application No. US2006/013621 entitled "Catheter Systems for Delivery of Agents and Related Method Thereof," filed Apr. 12, 2006.
56. U.S. patent application Ser. No. 11/105,166 entitled "Catheter Systems for Delivery of Agents and Related Method Thereof," filed Apr. 13, 2005; U.S. Pat. No. 7,670,327, issued Mar. 2, 2010.
57. U.S. patent application Ser. No. 10/985,340 entitled "Catheter Navigation Within an MR Imaging Device," filed Nov. 10, 2004.
58. U.S. patent application Ser. No. 10/429,524 entitled "Catheter Navigation Within an MR Imaging Device," filed May 5, 2003; U.S. Pat. No. 6,834,201, issued Dec. 21, 2004.
59. International Patent Application No. US02/02363 entitled "Catheter Navigation within an MR Imaging Device," filed Jan. 28, 2002.
60. U.S. patent application Ser. No. 09/772,188 entitled "Catheter Navigation within an MR Imaging Device," filed Jan. 29, 2001.
61. U.S. patent application Ser. No. 10/444,884 entitled "Cell Delivery Catheter and Method," filed May 23, 2003; U.S. Pat. No. 8,096,984, issued Jan. 17, 2012.
62. U.S. patent application Ser. No. 09/574,857 entitled "Cell Delivery Catheter and Method," filed May 19, 2000; U.S. Pat. No. 6,599,274, issued Jul. 29, 2003.
63. U.S. patent application Ser. No. 09/859,472 entitled "Continuous Metal Fiber Brushes," filed May 18, 2001.
64. U.S. patent application Ser. No. 09/147,100 entitled "Continuous Metal Fiber Brushes," filed Apr. 4, 1997; U.S. Pat. No. 6,245,440, issued Jun. 12, 2001.
65. International Patent Application No. US97/05149 entitled "CONTINUOUS METAL FIBER BRUSHES," filed Apr. 4, 1997.
65. U.S. patent application Ser. No. 09/548,110 entitled "Multi-Probe System," filed Apr. 12, 2000; U.S. Pat. No. 6,626,902, issued Sep. 30, 2003.
66. International Patent Application No. US99/24253 entitled "MRI AND MAGNETIC STEREOTAXIS SURGICAL SYSTEM," filed Oct. 15, 1999
67. U.S. patent application Ser. No. 09/174,189 entitled "Combined Magnetic Resonance Imaging and Magnetic Stereotaxis Surgical Apparatus and Processes," filed Oct. 16, 1998; U.S. Pat. No. 6,298,259, issued Oct. 2, 2001.

68. International Patent Application No. US99/17880 entitled "MR-Visible Device for Magnetic Stereotaxis Neurological Interventions," filed Aug. 6, 1999.
69. U.S. patent application Ser. No. 09/131,031 entitled "MR-Visible Medical Device for Neurological Interventions Using Nonlinear Magnetic Stereotaxis and a Method Imaging," filed Aug. 7, 1998;
70. U.S. Pat. No. 6,272,370, issued Aug. 7, 2001.
71. U.S. patent application Ser. No. 09/114,414 entitled "Magnetic Stereotactic System for Treatment Delivery," filed Jul. 13, 1998.
72. U.S. patent application Ser. No. 08/464,279 entitled "Magnetic Stereotactic System for Treatment Delivery," filed Jun. 5, 1995; U.S. Pat. No. 5,707,335, issued Jan. 13, 1998.
73. U.S. patent application Ser. No. 08/096,214 entitled "Magnetic Stereotactic System for Treatment Delivery," filed Jul. 19, 1993; U.S. Pat. No. 5,779,694, issued Jul. 14, 1998.
74. U.S. patent application Ser. No. 07/904,032 entitled "MAGNETIC STEREOTACTIC SYSTEM FOR TREATMENT DELIVERY," filed Jun. 25, 1992.
75. U.S. patent application Ser. No. 07/463,340 entitled "Magnetic Stereotactic System for Treatment Delivery," filed Jan. 10, 1990.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. A system for measuring the oxidation state of biological molecules in a region of a measurement site of a subject, said system comprising:

at least one emitter configured to be in optical communication with the region of the measurement site of the subject;

at least one detector configured to be in optical communication with the region of the measurement site of the subject;

wherein said at least one emitter or said at least one detector is configured to be disposed inside the subject;

said at least one emitter and said at least one detector are in electromagnetic radiation communication with one another, wherein the electromagnetic radiation communication allows visible radiation or near infrared radiation emitted by said at least one emitter to be detected by said at least one detector to determine tissue oxidation state of the region of the measurement site of the subject;

an interface member, wherein said interface member includes a proximal region, a distal region, and a longitudinal region there between;

an expandable component in mechanical communication with said interface member distal region, and said expandable component is located between said at least one emitter and said at least one detector and said interface member distal region;

wherein said expandable component is configured to assure that said at least one emitter and said at least one detector makes contact with tissue wall of the subject; and a processor configured to perform algorithmic steps to determine the tissue oxygenation ($StO_2$) of the region of the subject from detector data.

2. The system of claim 1, wherein both said at least one emitter and said at least one detector are configured to be disposed inside the subject.

3. The system of claim 1, wherein said expandable component includes at least one of the following: a balloon, expandable structure, stent, smart memory alloy (SMA) device, or inflatable compartment.

4. The system of claim 1, further comprises an electromagnetic radiation source in communication with said at least one emitter.

5. The system of claim 4, wherein said electromagnetic radiation source and said at least one emitter and said at least one detector comprises a visible-infrared or near-infrared spectroscopic system, or both a visible-infrared or near-infrared spectroscopic system.

6. The system of claim 1, wherein said at least one emitter and said at least one detector is in communication with a processor.

7. The system of claim 1, further comprising at least one port in communication with said interface member.

8. The system of claim 7, wherein said at least one port is configured for delivering cardioplegia solution.

9. The system of claim 1, wherein said interface member includes a distal tip, wherein said system further comprising at least one port disposed on said distal tip.

10. The system of claim 9, wherein said at least one port is configured for delivering cardioplegia solution.

11. The system of claim 1,
wherein said at least one emitter is in mechanical communication with said interface member.

12. The system of claim 11, wherein said interface member comprises a medical device.

13. The system of claim 12, wherein said medical device comprises a diagnostic or therapeutic device.

14. The system of claim 13, wherein said diagnostic device comprises a surgical device or a monitoring device.

15. The system of claim 12, wherein said medical device comprises a catheter.

16. The system of claim 12, wherein said medical device comprises at least one of the following: a substrate, probe, patch, drain, guidewire, tube, drainage tube, conduit, elongated member, lumen, circuit board, encapsulant, casing, packaging, housing, or membrane.

17. The system of claim 12, wherein said medical device comprise an ultrasound device.

18. The system of claim 12, further comprising:
an expandable component in mechanical communication with said medical device.

19. The system of claim 18, wherein said expandable component is configured to assure that said at least one emitter and said at least one detector makes contact with tissue wall of the subject.

20. The system of claim 18, wherein said expandable component includes at least one of the following: a balloon, expandable structure, stent, smart memory alloy (SMA) device, or inflatable compartment.

21. The system of claim 12, further comprising at least one port in communication with said medical device.

22. The system of claim 21, wherein said at least one port is configured for delivering cardioplegia solution.

23. The system of claim 12, wherein said medical device includes a distal tip, wherein said system further comprising at least one port disposed on said distal tip.

24. The system of claim 23, wherein said at least one port is configured for delivering cardioplegia solution.

25. The system of claim 1,
wherein said at least one detector is in mechanical communication with said interface member.

26. The system of claim 25, wherein said interface member comprises a medical device.

27. The system of claim 1,
wherein said at least one emitter and said at least one detector are in mechanical communication with said interface member.

28. The system of claim 27, wherein said interface member comprises a medical device.

29. The system of claim 1, wherein said at least one emitter being configured to make contact with the measurement site.

30. The system of claim 1, wherein said at least one detector being configured to make contact with the measurement site.

31. The system of claim 1, wherein said at least one emitter and said at least one detector are configured to make contact with the measurement site.

32. The method of claim 1, wherein the device is configured to measure the oxidation state of biological molecules that includes hemoglobin of blood.

33. The method of claim 1, wherein the device is configured to measure the oxidation state of biological molecules that includes at least one of myoglobin or cytochrome of the muscle or heart.

34. The method of claim 1, wherein the device is configured to measure the oxidation state of biological molecules that includes at least one of Hemoglobin or cytochrome of the heart.

35. The method of claim 1, wherein the device is configured to measure the oxidation state of biological molecules that includes at least one of Hemoglobin or cytochrome of an organ.

36. The system of claim 1, wherein:
said at least one emitter comprises a light emitting diode (LED); and
said at least one detector comprises photo detector.

37. The system of claim 1, wherein said tissue oxygenation ($StO_2$) of the region of the subject is accomplished using Beer-Lambert law or empirical derivation.

38. The system of claim 1, comprising:
at least two of said emitters; wherein one of said emitters is configured to emit the electromagnetic radiation at a high frequency so as to be above an isobestic point and one of said emitters is configured to emit the electromagnetic radiation at a low frequency so as to below the isobestic point; and
at least four of said detectors; said four detectors located in communication with said interface member so as to be at a known predetermined distance from respective said at least two emitters, whereby two of said detectors are provided for each of the referenced high and low frequencies of said emitters.

39. The system of claim 38, wherein said at least two emitters and said at least four detectors are in communication with the processor.

40. The system of claim 39, wherein the tissue oxygenation ($StO_2$) is determined by the execution of the following formula:

$$StO_2 = f(\text{high frequency}_{near}, \text{high frequency}_{far}, \text{low frequency}_{near}, \text{low frequency}_{far})$$

41. The system of claim 1, wherein said region is myocardium.

42. The system of claim 41, wherein said myocardium is located in the left ventricle of the heart.

43. A catheter system for measuring the oxidation state of biological molecules in a region of a measurement site of a subject, said system comprising:
a catheter device having a lumen, said catheter device includes proximal region, a distal region, and a longitudinal region there between;
at least one emitter in mechanical communication with said catheter distal region and configured to make contact with a tissue wall of the subject;
at least one detector in mechanical communication with said catheter distal region and configured to make contact with the tissue wall of the subject;
an expandable component in mechanical communication with said catheter distal region, and said expandable component is located between said at least one emitter and said at least one detector and said catheter distal region;

wherein said expandable component is configured to assure that said at least one emitter and said at least one detector makes contact with the tissue wall;

said at least one emitter and said at least one detector are in electromagnetic radiation communication with one another, wherein the electromagnetic radiation communication allows visible radiation or near infrared radiation emitted by said at least one emitter to be detected by said at least one detector to determine tissue oxidation state of the region of the measurement site of the subject; and a processor configured to perform algorithmic steps to determine the tissue oxygenation ($StO_2$) of the region of the subject from detector data.

44. The system of claim 43, wherein said expandable component includes at least one of the following: a balloon, expandable structure, stent, smart memory alloy (SMA) device, or inflatable compartment.

45. The system of claim 43, wherein the region of the measurement site is myocardium.

46. The system of claim 43, wherein the region of the measurement site is at least one of the following: blood, tissue, muscle, or organ.

47. A method for measuring the oxidation state of biological molecules in a region of a measurement site of a subject, said method comprising:
   providing at least one emitter in optical communication with the region of the measurement site of the subject;
   providing at least one detector in optical communication with the region of the measurement site of the subject;
   disposing said at least one emitter or said at least one detector inside the subject;
   communicating electromagnetic radiation between said at least one emitter and said at least one detector, wherein the electromagnetic radiation communication allows visible radiation or near infrared radiation emitted by said at least one emitter to be detected by said at least one detector to determine tissue oxidation state of the region of the measurement site of the subject;
   providing an interface member, wherein:
   said at least one emitter or said at least one detector is in mechanical communication with said an interface member; or
   both said at least one emitter and said at least one detector are in mechanical communication with said an interface member;
   providing an expandable component in mechanical communication with said interface member;
   wherein said expandable component is configured to assure that said at least one emitter and said at least one detector makes contact with tissue wall of the subject; and
   wherein said expandable component is in mechanical communication with said interface member distal region, and said expandable component is located between said at least one emitter and said at least one detector and said interface member distal region;
   further comprising communicating said at least one emitter and said at least one detector with a processor, and
   performing algorithmic steps using said processor to determine the tissue oxygenation ($StO_2$) of the region of the subject.

48. The method of claim 47, comprising:
   disposing both said at least one emitter and said at least one detector inside the subject.

49. The method of claim 47, wherein said expandable component includes at least one of the following: a balloon, expandable structure, stent, smart memory alloy (SMA) device, or inflatable compartment.

50. The method of claim 47, further comprises providing an electromagnetic radiation source in communication with said at least one emitter.

51. The method of claim 50, wherein said electromagnetic radiation source and said at least one emitter and said at least one detector comprises a visible-infrared or near-infrared spectroscopic system, or both a visible-infrared or near-infrared spectroscopic system.

52. The method of claim 47, further comprising at least one port in communication with said interface member.

53. The method of claim 52, wherein said at least one port is configured for delivering cardioplegia solution.

54. The method of claim 47, wherein said interface member includes a distal tip, wherein said system further comprising at least one port disposed on said distal tip.

55. The system of claim 54, wherein said at least one port is configured for delivering cardioplegia solution.

56. The method of claim 47, wherein said interface member comprises a medical device.

57. The method of claim 56, wherein said medical device comprises a diagnostic or therapeutic device.

58. The method of claim 57, wherein said diagnostic device comprises a surgical device or a monitoring device.

59. The method of claim 56, wherein said medical device comprises a catheter.

60. The method of claim 56, wherein said medical device comprises at least one of the following: a substrate, probe, patch, drain, guidewire, tube, drainage tube, conduit, elongated member, lumen, circuit board, encapsulant, casing, packaging, housing, or membrane.

61. The method of claim 56, wherein said medical device comprise an ultrasound device.

62. The method of claim 47, wherein said tissue oxygenation ($StO_2$) of the region of the subject is accomplished using Beer-Lambert law or empirical derivation.

63. A method for measuring the oxidation state of biological molecules in a region of a measurement site of a subject, said method comprising:
   providing a catheter device having a lumen, said catheter device includes proximal region, a distal regional, and a longitudinal region there between;
   providing at least one emitter configured to make contact with a tissue wall of the subject;
   providing at least one detector configured to make contact with the tissue wall of the subject;
   providing an expandable component in mechanical communication with said catheter distal region, and said expandable component is located between said at least one emitter and said at least one detector and said catheter distal region;
   communicating electromagnetic radiation between said at least one emitter and said at least one detector, wherein the electromagnetic radiation communication allows visible radiation or near infrared radiation emitted by said at least one emitters to be detected by said at least one detector to determine tissue oxidation state of the region of the measurement site of the subject; and
   performing algorithmic steps using a processor to determine the tissue oxygenation ($StO_2$) of the region of the subject.

64. The method of claim 63, further comprising:
   activating said expandable component to assure that said at least one emitter and said at least one detector makes contact with the tissue wall.

65. The method of claim 63, wherein said tissue oxygenation ($StO_2$) of the region of the subject is accomplished using Beer-Lambert law or empirical derivation.

66. The method of claim 63, comprising:
providing at least two of said emitters; wherein one of said emitters is configured to emit the electromagnetic radiation at a high frequency so as to be above an isobestic point and one of said emitters is configured to emit the electromagnetic radiation at a low frequency so as to below the isobestic point; and
providing at least four of said detectors; said four detectors located in communication with said catheter distal region so as to be at a known predetermined distance from respective said at least two emitters, whereby two of said detectors are provided for each of the referenced high and low frequencies of said emitters.

67. The method of claim 66, wherein said at least two emitters and said at least four detectors are in communication with a processor.

68. The method of claim 67, wherein said processor is configured to perform the algorithmic steps to determine the tissue oxygenation ($StO_2$) of the region of the subject.

69. The method of claim 68, wherein the tissue oxygenation ($StO_2$) is determined by the execution of the following formula:

$$StO_2 = f(\text{high frequency}_{near}, \text{high frequency}_{far}, \text{low frequency}_{near}, \text{low frequency}_{far}).$$

70. The method of claim 63, wherein said region is myocardium.

* * * * *